United States Patent
Horrell et al.

(10) Patent No.: US 9,138,219 B2
(45) Date of Patent: Sep. 22, 2015

(54) METHODS AND DEVICES FOR TREATING A SYNDESMOSIS INJURY

(75) Inventors: Chuck Horrell, San Francisco, CA (US); Paul M. Sand, Redwood City, CA (US); Peter Keith, Lanesboro, MN (US); Trevor Lofthouse, Sunnyvale, CA (US); Nick Mourlas, Mountain View, CA (US); John Avi Roop, Menlo Park, CA (US); Jason W. Lettmann, Menlo Park, CA (US)

(73) Assignee: Tarsus Medical Inc., Plainsboro, NJ (US)

( * ) Notice: Subject to any disclaimer, the term of this patent is extended or adjusted under 35 U.S.C. 154(b) by 329 days.

(21) Appl. No.: 13/183,818

(22) Filed: Jul. 15, 2011

(65) Prior Publication Data

US 2012/0172936 A1     Jul. 5, 2012

Related U.S. Application Data

(60) Provisional application No. 61/428,051, filed on Dec. 29, 2010.

(51) Int. Cl.
    *A61B 17/04*          (2006.01)
    *A61B 17/86*          (2006.01)
    (Continued)

(52) U.S. Cl.
    CPC ............ *A61B 17/0401* (2013.01); *A61B 17/86* (2013.01); *A61B 17/683* (2013.01);
    (Continued)

(58) Field of Classification Search
    CPC .. A61B 17/041; A61B 17/56; A61B 17/0401; A61B 17/86; A61B 17/8875; A61B 17/8891; A61F 2/4202; A61F 2002/4205; A61F 2002/421
    USPC ................... 606/300–321; 623/13.13–13.16
    See application file for complete search history.

(56) References Cited

U.S. PATENT DOCUMENTS

| 2,998,007 A | 5/1905 | Herzog |
| 2,236,079 A | 2/1940 | Wipper |

(Continued)

FOREIGN PATENT DOCUMENTS

| DE | 19612276 A1 | 10/1997 |
| DE | 29915204 U1 | 1/2000 |

(Continued)

OTHER PUBLICATIONS

Cottom, et al., "Treatment of Syndesmotic Disruptions with the Arthex Tightrope: A Report of 25 Cases," Foot and Ankle International, vol. 29, No. 8, pp. 773-780.

(Continued)

*Primary Examiner* — Matthew Lawson
*Assistant Examiner* — Si Ming Lee
(74) *Attorney, Agent, or Firm* — Eva Tan

(57) ABSTRACT

Embodiments relate to implantable devices for the treatment of syndesmosis injuries. Embodiments include a first anchor attachable to a first bone, the first anchor being coupled to a flexible component, the flexible component in turn being coupled to a base component. The base component may be rigid, and may be externally threaded for engaging with a second anchor. Position of the second anchor may be adjusted by rotating the second anchor with respect to the base component, thereby adjusting relative position of the two bones. An assembly may be created in which an outer tube contains the flexible component and the base component inside the outer tube, and at its distal end the outer tube may engage the first anchor so as to allow transmission of torque. The outer tube may be withdrawn proximally after implantation of the first anchor. The bones may be a tibia and a fibula.

24 Claims, 31 Drawing Sheets

(51) Int. Cl.
*A61F 2/08* (2006.01)
*A61B 17/80* (2006.01)
*A61B 17/56* (2006.01)
*A61F 2/42* (2006.01)
*A61B 17/68* (2006.01)
*A61B 17/84* (2006.01)
*A61B 17/88* (2006.01)

(52) U.S. Cl.
CPC ............ *A61B17/8061* (2013.01); *A61B 17/844* (2013.01); *A61B 17/8685* (2013.01); *A61B 17/8891* (2013.01); *A61B 2017/044* (2013.01); *A61B 2017/0409* (2013.01); *A61B 2017/0414* (2013.01); *A61B 2017/564* (2013.01); *A61F 2/4202* (2013.01)

(56) References Cited

U.S. PATENT DOCUMENTS

| | | |
|---|---|---|
| 2,291,413 A | 7/1942 | Siebrandt |
| 3,678,925 A | 7/1972 | Fischer et al. |
| 3,759,257 A | 9/1973 | Fischer et al. |
| 3,779,239 A | 12/1973 | Fischer et al. |
| 3,986,504 A | 10/1976 | Avila |
| 4,069,824 A | 1/1978 | Weinstock |
| 4,091,806 A | 5/1978 | Aginsky |
| 4,204,531 A | 5/1980 | Aginsky |
| 4,213,208 A | 7/1980 | Marne |
| 4,227,518 A | 10/1980 | Aginsky |
| 4,236,512 A | 12/1980 | Aginsky |
| 4,409,974 A | 10/1983 | Freedland |
| 4,453,539 A | 6/1984 | Raftopoulos et al. |
| 4,497,603 A | 2/1985 | Boucher et al. |
| 4,620,825 A | 11/1986 | Potzas |
| 4,632,100 A | 12/1986 | Somers et al. |
| 4,632,101 A | 12/1986 | Freedland |
| 4,721,103 A | 1/1988 | Freeland |
| 4,738,255 A | 4/1988 | Goble et al. |
| 4,859,128 A | 8/1989 | Brecz et al. |
| 4,947,502 A | 8/1990 | Engelhardt |
| 4,976,712 A | 12/1990 | VanderSlik |
| 5,037,422 A | 8/1991 | Hayhurst et al. |
| 5,044,850 A | 9/1991 | Getten et al. |
| 5,061,137 A | 10/1991 | Gourd |
| 5,067,956 A | 11/1991 | Buford, III et al. |
| 5,100,417 A | 3/1992 | Cerier et al. |
| 5,120,171 A | 6/1992 | Lasner |
| 5,139,499 A | 8/1992 | Small et al. |
| 5,141,520 A | 8/1992 | Goble et al. |
| 5,152,790 A | 10/1992 | Rosenberg et al. |
| 5,156,616 A | 10/1992 | Meadows et al. |
| 5,167,664 A | 12/1992 | Hodorek |
| 5,167,665 A | 12/1992 | McKinney |
| 5,192,303 A | 3/1993 | Gatturna et al. |
| 5,207,679 A | 5/1993 | Li |
| 5,217,462 A | 6/1993 | Asnis et al. |
| 5,226,766 A | 7/1993 | Lasner |
| 5,236,445 A | 8/1993 | Hayhurst et al. |
| 5,250,049 A | 10/1993 | Michael |
| 5,263,955 A | 11/1993 | Baumgart et al. |
| 5,268,000 A | 12/1993 | Ottieri et al. |
| 5,281,225 A | 1/1994 | Vicenzi |
| 5,306,301 A | 4/1994 | Graf et al. |
| 5,326,205 A | 7/1994 | Anspach, Jr. et al. |
| 5,350,383 A | 9/1994 | Schmieding et al. |
| 5,364,400 A | 11/1994 | Rego, Jr. et al. |
| 5,370,662 A | 12/1994 | Stone et al. |
| 5,411,523 A * | 5/1995 | Goble ........................ 606/232 |
| 5,437,674 A | 8/1995 | Worcel et al. |
| 5,443,482 A | 8/1995 | Stone et al. |
| 5,443,509 A | 8/1995 | Boucher et al. |
| 5,458,599 A | 10/1995 | Adobbati |
| 5,466,243 A | 11/1995 | Schmieding et al. |
| 5,470,334 A * | 11/1995 | Ross et al. .................... 606/916 |
| 5,472,452 A | 12/1995 | Trott |
| 5,480,403 A | 1/1996 | Lee et al. |
| 5,486,197 A | 1/1996 | Le et al. |
| 5,501,695 A | 3/1996 | Anspach, Jr. et al. |
| 5,503,510 A | 4/1996 | Golan |
| 5,520,696 A | 5/1996 | Wenstrom, Jr. |
| 5,522,845 A | 6/1996 | Wenstrom, Jr. |
| 5,529,075 A | 6/1996 | Clark |
| 5,569,306 A | 10/1996 | Thal |
| 5,571,104 A | 11/1996 | Li |
| 5,571,139 A | 11/1996 | Jenkins, Jr. |
| 5,573,548 A | 11/1996 | Nazre et al. |
| 5,578,035 A | 11/1996 | Lin |
| 5,584,629 A | 12/1996 | Bailey et al. |
| 5,584,835 A | 12/1996 | Greenfield |
| 5,584,860 A | 12/1996 | Goble |
| 5,601,565 A | 2/1997 | Huebner |
| 5,611,801 A | 3/1997 | Songer |
| 5,618,142 A | 4/1997 | Sonden et al. |
| 5,618,314 A | 4/1997 | Harwin et al. |
| 5,643,321 A | 7/1997 | McDevitt |
| 5,645,588 A | 7/1997 | Graf et al. |
| 5,649,963 A | 7/1997 | McDevitt |
| 5,665,112 A | 9/1997 | Thal |
| 5,690,677 A | 11/1997 | Schmieding et al. |
| 5,702,397 A | 12/1997 | Goble et al. |
| H1706 H | 1/1998 | Mason |
| 5,713,903 A | 2/1998 | Sander et al. |
| 5,713,904 A | 2/1998 | Errico et al. |
| 5,725,541 A | 3/1998 | Anspach, III et al. |
| 5,725,581 A | 3/1998 | Branemark |
| 5,725,585 A | 3/1998 | Zobel |
| 5,728,136 A | 3/1998 | Thal |
| 5,733,307 A | 3/1998 | Dinsdale |
| 5,735,898 A | 4/1998 | Branemark |
| 5,788,697 A | 8/1998 | Kilpela et al. |
| 5,797,913 A | 8/1998 | Dambreville et al. |
| 5,810,820 A | 9/1998 | Santori et al. |
| 5,810,822 A | 9/1998 | Mortier |
| 5,814,047 A | 9/1998 | Emilio et al. |
| 5,814,051 A | 9/1998 | Wenstrom, Jr. |
| 5,814,071 A | 9/1998 | McDevitt et al. |
| 5,824,011 A | 10/1998 | Stone et al. |
| 5,843,085 A | 12/1998 | Graser |
| 5,868,789 A | 2/1999 | Huebner |
| 5,879,352 A | 3/1999 | Filoso et al. |
| 5,882,351 A | 3/1999 | Fox |
| 5,893,850 A | 4/1999 | Cachia |
| 5,899,906 A | 5/1999 | Schenk |
| 5,919,194 A | 7/1999 | Anderson |
| 5,921,986 A | 7/1999 | Bonutti |
| 5,944,724 A | 8/1999 | Lizardi |
| 5,957,953 A | 9/1999 | DiPoto et al. |
| 5,964,783 A | 10/1999 | Grafton et al. |
| 5,971,986 A | 10/1999 | Santori et al. |
| 5,997,541 A | 12/1999 | Schenk |
| 6,001,101 A | 12/1999 | Augagneur et al. |
| 6,010,507 A | 1/2000 | Rudloff |
| 6,027,523 A | 2/2000 | Schmieding |
| 6,042,380 A | 3/2000 | De Rowe |
| 6,045,551 A | 4/2000 | Bonutti |
| 6,045,574 A | 4/2000 | Thal |
| 6,048,344 A | 4/2000 | Schenk |
| 6,068,648 A | 5/2000 | Cole et al. |
| 6,077,012 A | 6/2000 | Granese et al. |
| 6,117,160 A | 9/2000 | Bonutti |
| 6,117,162 A | 9/2000 | Schmieding et al. |
| 6,126,691 A | 10/2000 | Kasra et al. |
| 6,127,597 A | 10/2000 | Beyar et al. |
| 6,139,565 A | 10/2000 | Stone et al. |
| 6,149,669 A | 11/2000 | Li |
| 6,168,597 B1 | 1/2001 | Biedermann et al. |
| 6,187,008 B1 | 2/2001 | Hamman |
| 6,203,545 B1 | 3/2001 | Stoffella |
| 6,224,600 B1 | 5/2001 | Protogirou |
| 6,238,395 B1 | 5/2001 | Bonutti |
| 6,241,736 B1 | 6/2001 | Sater et al. |
| 6,248,109 B1 | 6/2001 | Stoffella |
| 6,261,289 B1 | 7/2001 | Levy |

(56) References Cited

U.S. PATENT DOCUMENTS

| | | |
|---|---|---|
| 6,264,677 B1 | 7/2001 | Simon et al. |
| 6,283,973 B1 | 9/2001 | Hubbard et al. |
| 6,287,310 B1 | 9/2001 | Fox |
| 6,299,398 B1 | 10/2001 | Shinjo |
| 6,319,255 B1 | 11/2001 | Grundei et al. |
| 6,319,270 B1 | 11/2001 | Grafton et al. |
| 6,328,758 B1 | 12/2001 | Tornier et al. |
| 6,348,053 B1 | 2/2002 | Cachia |
| 6,355,069 B1 | 3/2002 | DeCarlo, Jr. et al. |
| 6,368,326 B1 | 4/2002 | Dakin et al. |
| 6,406,234 B2 | 6/2002 | Frigg |
| 6,423,019 B1 | 7/2002 | Papay et al. |
| 6,475,242 B1 | 11/2002 | Bramlet |
| 6,506,190 B1 | 1/2003 | Walshe |
| 6,508,830 B2 | 1/2003 | Steiner |
| 6,511,481 B2 | 1/2003 | von Hoffmann et al. |
| 6,517,564 B1 | 2/2003 | Grafton et al. |
| 6,533,802 B2 | 3/2003 | Bojarski et al. |
| 6,540,770 B1 | 4/2003 | Tornier et al. |
| 6,547,792 B1 | 4/2003 | Tsuji et al. |
| 6,547,800 B2 | 4/2003 | Foerster et al. |
| 6,554,833 B2 | 4/2003 | Levy et al. |
| 6,558,388 B1 | 5/2003 | Bartsch et al. |
| 6,569,188 B2 | 5/2003 | Grafton et al. |
| 6,575,973 B1 | 6/2003 | Shekalim |
| 6,575,976 B2 | 6/2003 | Grafton |
| 6,582,453 B1 | 6/2003 | Tran et al. |
| 6,585,740 B2 | 7/2003 | Schlapfer et al. |
| 6,589,249 B2 | 7/2003 | Sater et al. |
| 6,599,295 B1 | 7/2003 | Tornier et al. |
| 6,616,665 B2 | 9/2003 | Grafton et al. |
| 6,623,492 B1 | 9/2003 | Berube et al. |
| 6,632,224 B2 | 10/2003 | Cachia et al. |
| 6,638,279 B2 | 10/2003 | Bonutti |
| 6,648,890 B2 | 11/2003 | Culbert et al. |
| 6,652,563 B2 | 11/2003 | Dreyfuss |
| 6,660,008 B1 | 12/2003 | Foerster et al. |
| 6,660,010 B2 | 12/2003 | Gellman |
| 6,666,877 B2 | 12/2003 | Morgan et al. |
| 6,685,706 B2 | 2/2004 | Padget et al. |
| 6,689,135 B2 | 2/2004 | Enayati |
| 6,689,136 B2 | 2/2004 | Stoffella |
| 6,716,234 B2 | 4/2004 | Grafton |
| 6,736,818 B2 | 5/2004 | Perren et al. |
| 6,736,819 B2 | 5/2004 | Tipirneni |
| 6,749,384 B1 | 6/2004 | Ellis |
| 6,783,530 B1 | 8/2004 | Levy |
| 6,860,017 B1 | 3/2005 | Mennicken |
| 6,887,243 B2 | 5/2005 | Culbert |
| 6,887,259 B2 | 5/2005 | Lizardi |
| 6,890,333 B2 | 5/2005 | von Hoffmann et al. |
| 6,893,446 B2 | 5/2005 | Sater et al. |
| 6,905,296 B2 | 6/2005 | Millington |
| 6,908,275 B2 | 6/2005 | Nelson et al. |
| 6,908,465 B2 | 6/2005 | von Hoffmann et al. |
| 6,923,824 B2 | 8/2005 | Morgan et al. |
| 6,936,052 B2 | 8/2005 | Gellman et al. |
| 6,942,668 B2 | 9/2005 | Padget et al. |
| 6,951,561 B2 | 10/2005 | Warren et al. |
| 6,991,597 B2 | 1/2006 | Gellman et al. |
| 6,991,636 B2 | 1/2006 | Rose |
| 6,997,940 B2 | 2/2006 | Bonutti |
| 7,008,428 B2 | 3/2006 | Cachia et al. |
| 7,052,498 B2 | 5/2006 | Levy et al. |
| 7,056,333 B2 | 6/2006 | Walshe |
| 7,070,601 B2 | 7/2006 | Culbert et al. |
| 7,090,690 B2 | 8/2006 | Foerster et al. |
| 7,097,654 B2 | 8/2006 | Freedland |
| 7,175,626 B2 | 2/2007 | Neff |
| 7,182,561 B2 | 2/2007 | Jones |
| 7,182,566 B1 | 2/2007 | Nelson et al. |
| 7,217,293 B2 | 5/2007 | Branch, Jr. |
| 7,226,469 B2 | 6/2007 | Benavitz et al. |
| 7,235,091 B2 | 6/2007 | Thornes |
| 7,273,338 B2 | 9/2007 | Summerlin |
| 7,322,783 B2 | 1/2008 | Pearce et al. |
| 7,322,978 B2 | 1/2008 | West, Jr. |
| 7,325,323 B2 | 2/2008 | Katsu et al. |
| 7,326,211 B2 | 2/2008 | Padget et al. |
| 7,384,226 B2 | 6/2008 | Jones et al. |
| 7,410,489 B2 | 8/2008 | Dakin et al. |
| 7,481,825 B2 | 1/2009 | Bonutti |
| 7,485,135 B2 | 2/2009 | Steiger et al. |
| 7,500,983 B1 | 3/2009 | Kaiser |
| 7,507,241 B2 | 3/2009 | Levy et al. |
| 7,556,629 B2 | 7/2009 | von Hoffmann et al. |
| 7,578,825 B2 | 8/2009 | Huebner |
| 7,588,587 B2 | 9/2009 | Barbieri et al. |
| 7,591,823 B2 | 9/2009 | Tipirneni |
| 7,601,152 B2 | 10/2009 | Levy et al. |
| 7,601,165 B2 | 10/2009 | Stone |
| 7,608,098 B1 | 10/2009 | Stone et al. |
| 7,625,395 B2 * | 12/2009 | Muckter ........................ 606/300 |
| 7,650,681 B2 | 1/2010 | Jones et al. |
| 7,670,339 B2 | 3/2010 | Levy et al. |
| 7,678,138 B2 | 3/2010 | Fitt et al. |
| 7,686,807 B2 | 3/2010 | Padget et al. |
| 7,722,303 B2 | 5/2010 | Williams |
| 7,749,250 B2 | 7/2010 | Stone et al. |
| 7,824,141 B2 | 11/2010 | Jones et al. |
| 7,824,429 B2 | 11/2010 | Culbert et al. |
| 7,833,255 B2 | 11/2010 | Chow et al. |
| 7,857,830 B2 | 12/2010 | Stone et al. |
| 7,875,058 B2 | 1/2011 | Holmes, Jr. |
| 7,901,412 B2 | 3/2011 | Tipirneni |
| 7,901,431 B2 | 3/2011 | Shurnas |
| 7,905,903 B2 | 3/2011 | Stone et al. |
| 7,905,904 B2 | 3/2011 | Stone et al. |
| 7,905,908 B2 | 3/2011 | Cragg et al. |
| 7,909,851 B2 | 3/2011 | Stone et al. |
| 7,938,836 B2 | 5/2011 | Ainsworth et al. |
| 7,951,198 B2 | 5/2011 | Sucec et al. |
| 7,955,388 B2 | 6/2011 | Jensen et al. |
| 7,959,681 B2 | 6/2011 | Lavi |
| 8,048,134 B2 | 11/2011 | Partin |
| 8,062,298 B2 | 11/2011 | Schmitz et al. |
| 8,066,748 B2 | 11/2011 | Lieberman et al. |
| 8,096,742 B2 | 1/2012 | Davies et al. |
| 8,114,127 B2 | 2/2012 | West, Jr. et al. |
| 8,114,128 B2 | 2/2012 | Cauldwell et al. |
| 8,114,141 B2 | 2/2012 | Appenzeller et al. |
| 8,118,835 B2 | 2/2012 | Weisel |
| 8,118,836 B2 | 2/2012 | Denham et al. |
| 8,128,658 B2 | 3/2012 | Kaiser et al. |
| 8,137,382 B2 | 3/2012 | Denham et al. |
| 8,147,514 B2 | 4/2012 | Bonutti |
| 8,197,523 B2 | 6/2012 | Bottlang |
| 8,221,455 B2 | 7/2012 | Shurnas et al. |
| 8,221,478 B2 | 7/2012 | Patterson et al. |
| 8,221,502 B2 | 7/2012 | Branch, Jr. |
| 8,231,674 B2 | 7/2012 | Albertorio |
| 8,246,661 B2 | 8/2012 | Beutter et al. |
| 8,277,459 B2 | 10/2012 | Sand et al. |
| 8,328,806 B2 | 12/2012 | Tyber et al. |
| 8,343,186 B2 | 1/2013 | Dreyfuss et al. |
| 8,382,810 B2 | 2/2013 | Peterson et al. |
| 8,388,667 B2 * | 3/2013 | Reiley et al. .................. 606/300 |
| 8,439,976 B2 | 5/2013 | Albertori et al. |
| 8,484,001 B2 | 7/2013 | Glozman et al. |
| 8,512,376 B2 | 8/2013 | Thornes |
| 8,551,094 B2 | 10/2013 | von Hoffmann et al. |
| 8,597,337 B2 | 12/2013 | Champagne |
| 2002/0188297 A1 * | 12/2002 | Dakin et al. .................... 606/72 |
| 2002/0198527 A1 | 12/2002 | Muckter |
| 2003/0045881 A1 | 3/2003 | Barouk et al. |
| 2003/0130660 A1 | 7/2003 | Levy et al. |
| 2004/0071522 A1 | 4/2004 | Millington |
| 2004/0127907 A1 | 7/2004 | Dakin et al. |
| 2004/0133204 A1 | 7/2004 | Davies |
| 2004/0210234 A1 | 10/2004 | Coillard-Lavirotte |
| 2005/0131411 A1 | 6/2005 | Culbert |
| 2005/0137595 A1 | 6/2005 | Hoffmann et al. |
| 2005/0159749 A1 | 7/2005 | Levy et al. |
| 2005/0177163 A1 * | 8/2005 | Abdou ............................ 606/72 |

(56) References Cited

U.S. PATENT DOCUMENTS

| | | |
|---|---|---|
| 2005/0177167 A1* | 8/2005 | Muckter .................. 606/73 |
| 2005/0197711 A1 | 9/2005 | Cachia |
| 2005/0222618 A1 | 10/2005 | Dreyfuss et al. |
| 2005/0228391 A1 | 10/2005 | Levy et al. |
| 2005/0229433 A1 | 10/2005 | Cachia |
| 2005/0267479 A1 | 12/2005 | Morgan et al. |
| 2006/0015102 A1 | 1/2006 | Toullec et al. |
| 2006/0030854 A1 | 2/2006 | Haines |
| 2006/0058796 A1 | 3/2006 | Hartdegen et al. |
| 2006/0100630 A1 | 5/2006 | West, Jr. |
| 2006/0178702 A1 | 8/2006 | Pierce et al. |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2006/0282081 A1 | 12/2006 | Fanton et al. |
| 2007/0010818 A1 | 1/2007 | Stone et al. |
| 2007/0016208 A1 | 1/2007 | Thornes |
| 2007/0060922 A1 | 3/2007 | Dreyfuss |
| 2007/0073299 A1 | 3/2007 | Dreyfuss et al. |
| 2007/0162018 A1* | 7/2007 | Jensen et al. .............. 606/69 |
| 2007/0179531 A1 | 8/2007 | Thornes |
| 2007/0260252 A1 | 11/2007 | Schmitz et al. |
| 2007/0265634 A1 | 11/2007 | Weinstein |
| 2007/0270855 A1 | 11/2007 | Partin |
| 2007/0282342 A1 | 12/2007 | Niederberger et al. |
| 2007/0299382 A1 | 12/2007 | Millet |
| 2008/0041169 A1 | 2/2008 | Walczyk et al. |
| 2008/0065224 A1 | 3/2008 | Reigstad et al. |
| 2008/0086139 A1 | 4/2008 | Bourke et al. |
| 2008/0147084 A1 | 6/2008 | Bleich et al. |
| 2008/0177291 A1* | 7/2008 | Jensen et al. ............. 606/151 |
| 2008/0200989 A1 | 8/2008 | Cachia |
| 2008/0208252 A1 | 8/2008 | Holmes |
| 2008/0221697 A1 | 9/2008 | Graser |
| 2008/0294170 A1 | 11/2008 | O'Brien |
| 2009/0036893 A1 | 2/2009 | Kartalian et al. |
| 2009/0043318 A1 | 2/2009 | Michel et al. |
| 2009/0062868 A1 | 3/2009 | Casutt |
| 2009/0069813 A1 | 3/2009 | von Hoffmann et al. |
| 2009/0082773 A1 | 3/2009 | Haines |
| 2009/0082874 A1 | 3/2009 | Cachia |
| 2009/0112269 A1 | 4/2009 | Lieberman et al. |
| 2009/0138014 A1 | 5/2009 | Bonutti |
| 2009/0149889 A1 | 6/2009 | Peterson et al. |
| 2009/0157194 A1 | 6/2009 | Shikinami |
| 2009/0198287 A1 | 8/2009 | Chiu |
| 2009/0210010 A1 | 8/2009 | Strnad et al. |
| 2009/0210016 A1 | 8/2009 | Champagne |
| 2009/0216334 A1 | 8/2009 | Leibel |
| 2009/0222047 A1 | 9/2009 | Graham |
| 2009/0228049 A1 | 9/2009 | Park |
| 2009/0287246 A1 | 11/2009 | Cauldwell et al. |
| 2009/0291975 A1 | 11/2009 | Stern et al. |
| 2009/0306723 A1 | 12/2009 | Anapliotis et al. |
| 2010/0036430 A1 | 2/2010 | Hartdegen et al. |
| 2010/0082072 A1 | 4/2010 | Sybert et al. |
| 2010/0152752 A1 | 6/2010 | Denove et al. |
| 2010/0191284 A1 | 7/2010 | Dreyfuss et al. |
| 2010/0211071 A1 | 8/2010 | Lettmann et al. |
| 2010/0256677 A1 | 10/2010 | Albertorio et al. |
| 2010/0262185 A1 | 10/2010 | Gelfand et al. |
| 2010/0275743 A1 | 11/2010 | Wengreen et al. |
| 2011/0066156 A1 | 3/2011 | Mcgahan et al. |
| 2011/0077656 A1 | 3/2011 | Sand et al. |
| 2011/0118780 A1 | 5/2011 | Holmes, Jr. |
| 2011/0137341 A1 | 6/2011 | Thornes et al. |
| 2011/0178557 A1 | 7/2011 | Rush et al. |
| 2011/0224729 A1 | 9/2011 | Baker et al. |
| 2011/0301648 A1 | 12/2011 | Lofthouse et al. |
| 2012/0016426 A1 | 1/2012 | Robinson |
| 2012/0071935 A1 | 3/2012 | Keith et al. |
| 2012/0123474 A1 | 5/2012 | Zajac et al. |
| 2012/0277795 A1 | 11/2012 | Von Hoffmann et al. |
| 2012/0330322 A1 | 12/2012 | Sand et al. |

FOREIGN PATENT DOCUMENTS

| | | |
|---|---|---|
| EP | 0374088 A1 | 10/1989 |
| EP | 0738502 B1 | 10/1996 |
| EP | 0882431 A1 | 12/1998 |
| EP | 0922437 A1 | 6/1999 |
| EP | 1273269 B1 | 1/2007 |
| EP | 1836981 A2 | 9/2007 |
| FR | 2653006 A1 | 4/1991 |
| FR | 2741256 A1 | 5/1997 |
| FR | 2745999 A1 | 9/1997 |
| FR | 2784019 B3 | 4/2000 |
| FR | 2893496 A1 | 5/2007 |
| GB | 2173565 A1 | 10/1986 |
| JP | 08052156 | 2/1996 |
| WO | WO 0018313 | 4/2000 |
| WO | WO 0044946 | 8/2000 |
| WO | WO 0128443 A1 | 4/2001 |
| WO | WO 0134045 A1 | 5/2001 |
| WO | WO 02058575 A1 | 8/2002 |
| WO | WO 03007830 A1 | 1/2003 |
| WO | WO 2004078220 A2 | 9/2004 |
| WO | WO 2005070314 A1 | 8/2005 |
| WO | WO 2005096975 A2 | 10/2005 |
| WO | WO 2006084994 A1 | 8/2006 |
| WO | WO 2007063399 A1 | 6/2007 |
| WO | WO 2009018527 A1 | 2/2009 |
| WO | WO 2010093696 A1 | 8/2010 |

OTHER PUBLICATIONS

Peter, et al., "Biochemical Effects of Internal Fixation of the Distal Tibiofibular Syndesmotic Joint: Comparision of Two Fixation Techniques," Journal of Orthopedic Trauma, vol. 8, No. 3, pp. 215-219 (1994).

West, "Mini TightRope System for Hallux Adbucto Vallux Valgus Deformity," Journal of the American Podiatric Association, vol. 100, No. 4, pp. 291-295 (2010).

* cited by examiner

METHODS AND DEVICES FOR TREATING A SYNDESMOSIS INJURY

CROSS-REFERENCE TO RELATED APPLICATIONS

This application claims priority to U.S. Provisional Application 61/428,051, filed Dec. 29, 2010 and entitled "Bone Approximation Devices and Methods," which is hereby incorporated herein by reference in its entirety.

FIELD OF THE INVENTION

The various embodiments disclosed herein relate to methods and devices for treating a syndesmosis injury. Certain specific embodiments relate to systems and methods for correcting such an injury, including an ankle syndesmosis injury.

BACKGROUND OF THE INVENTION

A syndesmosis is a type of joint. More specifically, a syndesmosis is a slightly movable articulation where contiguous bony surfaces are united by an interosseous ligament. An example is the inferior tibiofibular articulation of the ankle. This syndesmosis is made up of the anterior tibiofibular ligament, the interosseous ligament, and the posterior-fibular ligaments. Following trauma to the ankle, such as an ankle fracture, the syndesmotic joint can become unstable and painful. FIG. 1A depicts an exemplary type of ankle fractures that can result in a syndesmotic joint injury. It is also understood that syndesmosis injury can also occur without fracture, such as with a severe ankle sprain. An example of this type of syndesmosis injury is depicted in FIG. 1B, in which the ligaments have been torn without any bone fracture. The syndesmosis is identified in FIGS. 1A and 1B using the number "5." Surgery may be needed to stabilize the syndesmotic joint to allow these ligaments to properly heal. The current standard of care involves fixing the fibula to the tibia during the soft tissue healing process with one or two screws. Because these screws can inhibit normal joint motion, the screws are typically removed after the ligament injury is healed.

There is a need in the art for improved methods and devices for treating syndesmosis injuries, including ankle syndesmosis injuries.

BRIEF SUMMARY OF THE INVENTION

Discussed herein are various treatment devices for treating syndesmosis injuries.

In Example 1, a method of treating a syndesmosis injury comprises positioning a first bone anchor through a second bone and into a first bone, wherein the first bone anchor is coupled to a first end of a tether, attaching the first bone anchor within the first bone, positioning a second bone anchor in the second bone and coupling the second bone anchor to a second end of the tether, urging the second bone anchor distally in relation to the tether with an anchor placement tool and thereby urging the second bone anchor toward the first bone anchor, examining a radiographic image to determine the initial position of the second bone in relation to the first bone, adjusting the positioning of the second bone anchor based on the initial position of the second bone in relation to the first bone to achieve a desired position, and removing the anchor placement tool.

Example 2 relates to the method of treating a syndesmosis injury according to Example 1, wherein attaching the first bone anchor with the first bone further comprises deploying prongs within the first bone, wherein the prongs are operably coupled to the first bone anchor.

Example 3 relates to the method of treating a syndesmosis injury according to Example 1, wherein urging the second bone anchor distally in relation to the tether further comprises rotating the anchor placement tool and thereby rotating the second bone anchor.

Example 4 relates to the method of treating a syndesmosis injury according to Example 1, wherein positioning a first bone anchor further comprises positioning a deployment assembly through a hole formed in the second bone and into contact with the first bone. The deployment assembly comprises an outer tube, the tether disposed within the outer tube, the tether comprising a flexible component and a base component coupled to the flexible component, the first bone anchor disposed at the distal end of the outer tube, the first bone anchor being coupled to the first end of the flexible component, and a deployment tube disposed within the outer tube, the deployment tube comprising a deployment anvil disposed at the distal end of the deployment tube.

Example 5 relates to the method of treating a syndesmosis injury according to Example 4, wherein the deploying the prongs comprises urging the deployment tube in a proximal direction in relation to the outer tube, whereby the deployment anvil is urged against the first bone anchor.

Example 6 relates to the method of treating a syndesmosis injury according to Example 3, wherein the coupling the second bone anchor to the second end of the tether further comprises coupling the second bone anchor to a proximal end of the base component.

Example 7 relates to the method of treating a syndesmosis injury according to Example 5, wherein the coupling the second bone anchor to the proximal end of the base component further comprises using an anchor placement tool to couple the second bone anchor to the proximal end of the base component.

Example 8 relates to the method of treating a syndesmosis injury according to Example 1, the method further comprising forming a hole in the second bone prior to positioning the first bone anchor in the first bone.

Example 9 relates to the method of treating a syndesmosis injury according to Example 1, the method further comprising first positioning a guide wire through the second bone and into the first bone, wherein the positioning the first bone anchor comprises positioning the first bone anchor over the guide wire.

Example 10 relates to the method of treating a syndesmosis injury according to Example 1, wherein positioning the first bone anchor into the first bone further comprises positioning the first bone anchor into the first bone such that a proximal end of the first bone anchor is substantially flush with a surface of the first bone.

In Example 11, a method of treating a syndesmosis injury comprises positioning a first bone anchor through a second bone and into a first bone, wherein the first bone anchor is coupled to a first end of a tether, attaching the first bone anchor within the first bone, positioning a second bone anchor in the second bone and coupling the second bone anchor to a second end of the tether, urging the second bone anchor distally in relation to the tether with an anchor placement tool and thereby urging the second bone anchor toward the first bone anchor, evaluating ankle function to determine the initial position of the second bone in relation to the first bone, adjusting the positioning of the second bone anchor based on the initial position of the second bone in relation to the first bone to achieve a desired position, and removing the anchor placement tool.

In Example 12, a method of treating a syndesmosis injury comprises forming a hole through a second bone and into a first bone, inserting a deployment assembly into the hole in the second bone, positioning the first bone anchor in the first bone, removing the deployment assembly, and coupling a second bone anchor to a second end of the tether and positioning the second bone anchor in the second bone. The deployment assembly comprises an outer tube, a tether disposed within the outer tube, and a first bone anchor disposed at the distal end of the outer tube, the first bone anchor being coupled to the first end of the flexible component. The tether comprises a flexible component, and a base component coupled to the flexible component.

Example 13 relates to the method of treating a syndesmosis injury according to Example 12, wherein the positioning the first bone anchor further comprises rotating the deployment assembly to drill the first bone anchor into the first bone.

Example 14 relates to the method of treating a syndesmosis injury according to Example 12, further comprising urging the second bone anchor distally in relation to the tether, thereby urging the second bone anchor toward the first bone anchor.

Example 15 relates to the method of treating a syndesmosis injury according to Example 12, further comprising first positioning a guide wire through the second bone and into the first bone, wherein the forming the hole in the second bone further comprises positioning a drill over the guide wire and drilling the hole in the second bone, and wherein the inserting the deployment assembly into the hole further comprises inserting the deployment assembly over the guide wire.

In Example 16, a method of treating a syndesmosis injury comprises forming a hole through a fibula bone and into a tibia bone, inserting a deployment assembly into the hole in the fibula bone, positioning the first bone anchor in the tibia bone using the deployment assembly, removing the deployment assembly, and coupling a second bone anchor to a second end of the tether and positioning the second bone anchor in the fibula bone. The deployment assembly comprises an outer tube comprising at least two prongs at a distal end of the outer tube, a tether disposed within the outer tube, and a first bone anchor disposed at the distal end of the outer tube. The tether comprises a flexible component and a base component coupled to the flexible component. The first bone anchor comprises external threads defined on an external portion of the first bone anchor, and at least two openings defined in the threads at a proximal end of the first bone anchor, the at least two openings configured to receive the at least two prongs of the outer tube.

Example 17 relates to the method of treating a syndesmosis injury according to Example 16, wherein the external threads are defined on substantially all of the external portion of the first bone anchor.

Example 18 relates to the method of treating a syndesmosis injury according to Example 16, further comprising positioning the second bone anchor with an anchor placement tool, examining a radiographic image or evaluating ankle function to determine the initial position of the second bone in relation to the first bone, adjusting the positioning of the second bone anchor based on the initial position of the second bone in relation to the first bone to achieve a desired position, and removing the anchor placement tool.

Example 19 relates to the method of treating a syndesmosis injury according to Example 18, wherein the positioning and the adjusting of the positioning of the second bone anchor comprises rotating the anchor placement tool and thereby rotating the second bone anchor.

Example 20 relates to the method of treating a syndesmosis injury according to Example 16, wherein the second bone anchor comprises a head comprising at least two openings.

Example 21 relates to the method of treating a syndesmosis injury according to Example 20, wherein the anchor placement tool comprises at least two prongs configured to be positionable within the at least two openings in the head of the second bone anchor.

In Example 22, a method of treating a syndesmosis injury comprises positioning a first bone anchor through a second bone and into a first bone, wherein the first bone anchor is coupled to a first end of a tether, urging the first bone anchor into the first bone with a deployment tool, positioning a second bone anchor in the second bone and coupling the second bone anchor to a second end of the tether, and urging the second bone anchor distally in relation to the tether with an anchor placement tool, thereby urging the second bone anchor toward the first bone anchor until the second bone anchor is positioned as desired. The first bone anchor comprises external threads defined along an entire length of an external portion of the first bone anchor, wherein the external threads are configured to be engageable with a cortical surface of the first bone, and at least two openings defined in the external threads at a proximal end of the first bone anchor, the at least two openings configured to receive at least two prongs of the deployment tool.

Example 23 relates to the method of treating a syndesmosis injury according to Example 22, wherein the first bone anchor further comprises a lumen defined within the first bone anchor, and a opening at a distal end of the first bone anchor, wherein the opening is in communication with the lumen, and further wherein the urging the first bone anchor into the first bone with the deployment tool further comprises urging the first bone anchor into the first bone without operably coupling the deployment tool with the opening or the lumen.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Various embodiments disclosed herein relate to methods and devices for treating a syndesmosis injury, such as, for example, an ankle syndesmosis injury. More specifically, various embodiments herein relate to syndesmosis injury treatments using tension or connection systems and methods for anchoring or otherwise coupling bones such as the tibia and fibula bones. Some of the various device and method embodiments disclosed herein operate at least in part by anchoring or coupling to the tibia and fibula bones. While various embodiments as described herein relate to the ankle syndesmosis joint, it is understood that the embodiments can also apply to other syndesmosis joints in the body, including those existing in the wrist, forearm, spine and shoulder.

Various prior art screws are too rigid for permanent implantation and thus are often removed. Other prior art devices (such as, for example, the Tight Rope™ system available from Arthrex) can be flexible enough that removal is not required, but are not secure enough during the acute healing phase to provide optimal healing. In contrast, certain of the implant embodiments described and/or contemplated herein can remain in the patient's body permanently. Some embodiments provide substantially secure fixation during the healing period but do not cause long-term binding of the joint. Other embodiments provide an implanted fixation system that is either flush with, or internal to, the cortical bone. Certain implementations also allow the surgeon to adjust the spacing between the tibia and fibula after implantation. As such, various embodiments disclosed herein provide systems and methods for implantation of treatment devices and treatment of ankle syndesmosis injuries with reduced trauma and quicker recovery in comparison to known systems and treatments.

Figure 1A:
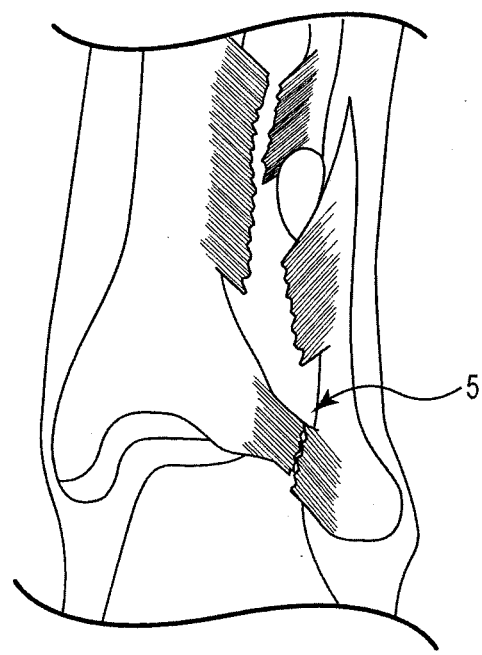
FIG. 1A is a schematic depiction of a syndesmosis injury with a bone fracture.
Figure 1B:
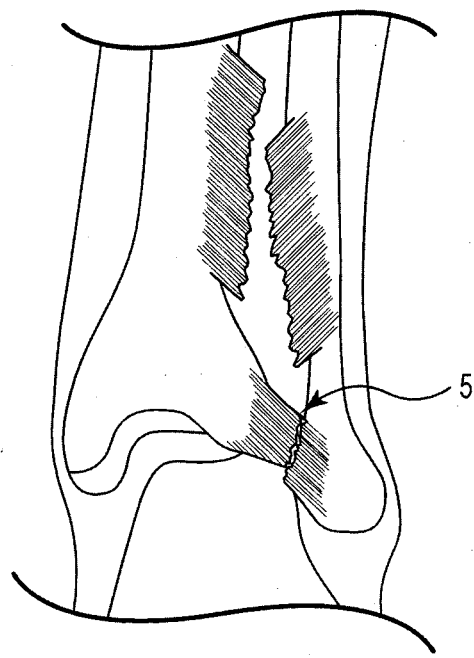
FIG. 1B is a schematic depiction of a syndesmosis injury without a fracture.
Figure 2:
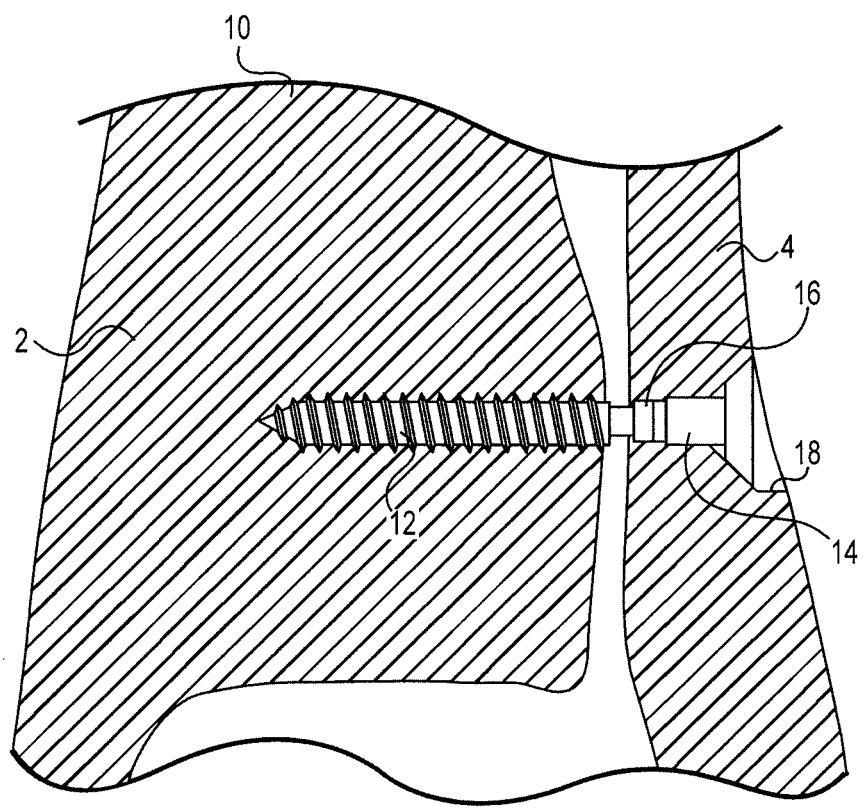
FIG. 2 is a schematic depiction of an implantable syndesmosis injury treatment device implanted in a patient, according to one embodiment.
Figure 5A:
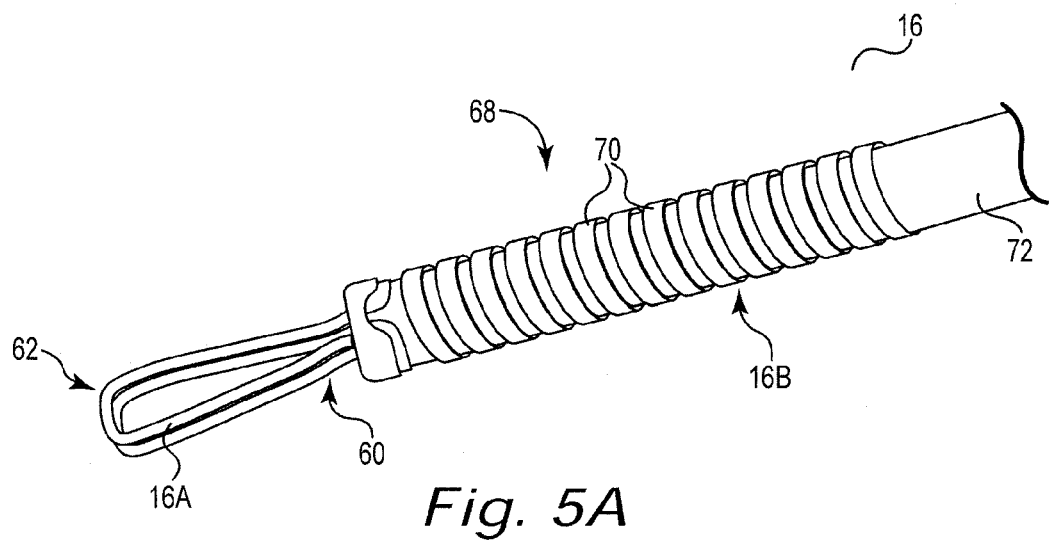
FIG. 5A is a side view of a tether, according to one embodiment.

One embodiment of a syndesmosis repair device 10 is depicted in FIG. 2. In this embodiment, the device or system 10 couples the tibia 2 and fibula 4 bones of a human leg. As shown in the figure, the device 10 is an implant having a first anchor 12 positioned in the tibia 2, a second anchor 14 positioned in the fibula 4, and a tether 16 coupled to or coupling the first anchor 12 to the second anchor 14. According to the specific implementation in FIG. 2, the first anchor 12 is an externally threaded anchor 12 embedded in the tibia 2 and the second anchor 14 is an internally threaded anchor threadably coupled to the tether 16 and positioned within a countersunk hole 18 drilled in the fibula 4. As best shown in FIG. 5A in combination with FIG. 2, the tether 16 in this implementation has a flexible component 16A and a cylindrical base component 16B, wherein the flexible component 16A is at least one suture 16A coupled to the first anchor 12 and the cylindrical base component 16B at one end is coupled to the at least one suture 16A and at the other end is threadably coupled to the second anchor 14.

In this embodiment, the anchors 12, 14 are strategically embedded within the tibia 2 and fibular to urge the two bones together, thereby correcting or otherwise treating an ankle syndesmosis injury. Alternatively, it is understood that the anchors 12, 14 can be positioned anywhere along any two bones to treat a syndesmosis injury. Further, as discussed above, in the depicted embodiment the first anchor 12 is an externally threaded bone anchor 12 and the second anchor 14 is an internally-threaded bone anchor 14. Alternatively, the anchors 12, 14 can take a variety of different forms as contemplated herein, including several discussed below, without departing from the spirit of the invention. In addition, as noted above, the implementation as shown in FIG. 2 and FIG. 5A includes a tether 16 having a flexible component 16A comprised of at least one suture 16A and a cylindrical base component 16B. Alternatively, the tether 16 can take a variety of known forms.

It is understood that each of the various device and method embodiments disclosed herein can be the sole treatment for the syndesmosis injury. It is further understood that any of these embodiments could also be used in conjunction with any one or more of other known treatments, such as plates and/or screws associated with bone fracture(s).

It is understood that the term "bone anchor" (or, alternatively, "anchor"), as used herein, is intended for purposes of this application to mean any component or device that can be used with any of the treatment device embodiments disclosed herein for anchoring or coupling such treatment devices to a bone. It is also understood that "tether," as used herein, is intended to mean any elongate component for use with medical devices such as suture, thread, a tube, or any other such material or device or combination thereof that can couple or be tensioned between two components such as anchors to treat syndesmosis injuries. In addition, it is understood that "prong," as used herein, is intended for purposes of this application to mean any component or device that projects or extends from a bone anchor and is intended to enhance fixation of the anchor in the bone.

Figure 3A:
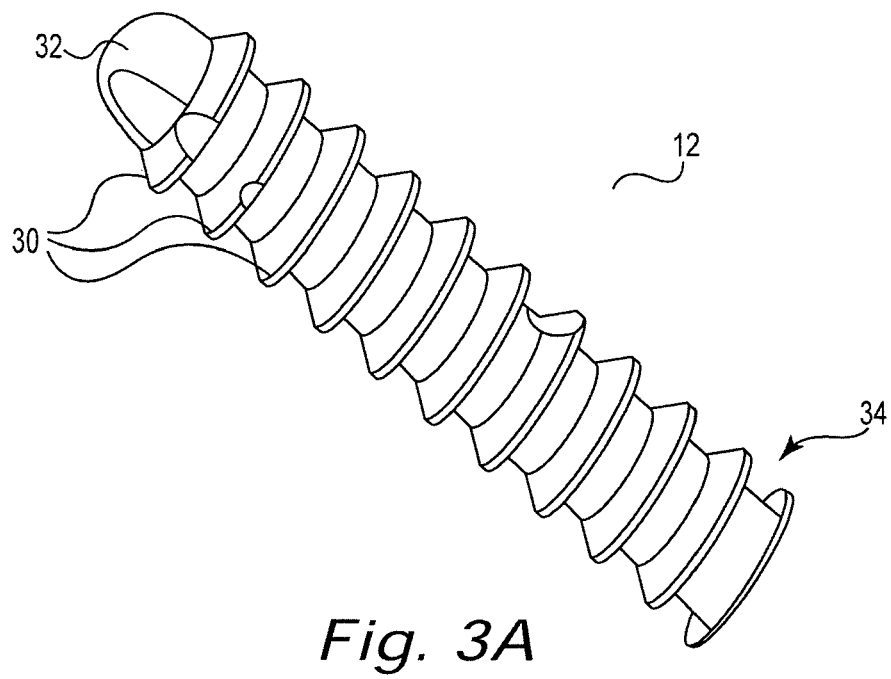
FIG. 3A is a side view of a first anchor, according to one embodiment.
Figure 3B:
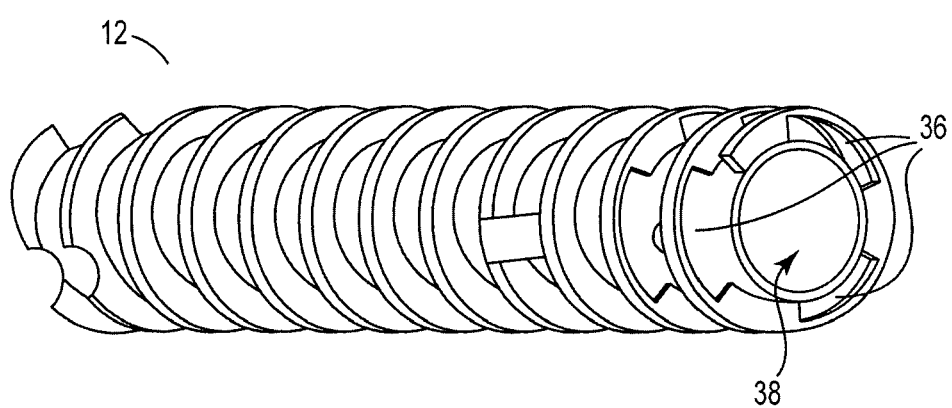
FIG. 3B is a perspective view of the first anchor of FIG. 3A, according to one embodiment.
Figure 3C:
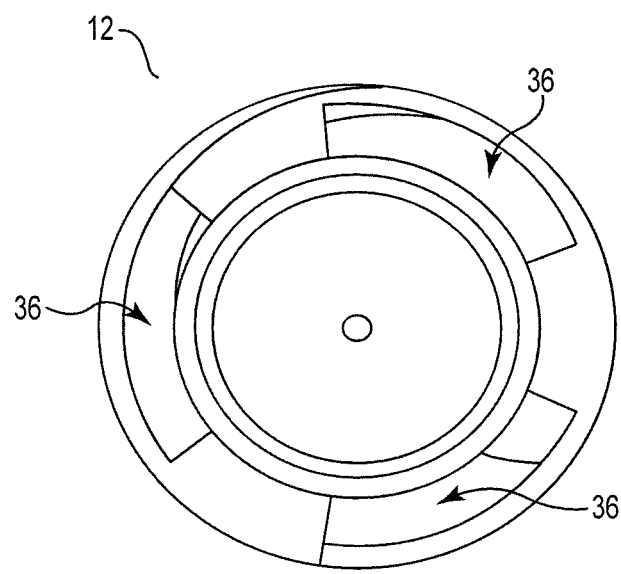
FIG. 3C is a rear view of the first anchor of FIG. 3A, according to one embodiment.

One embodiment of a first anchor 12 is depicted in FIGS. 3A-3C. In this implementation, the anchor 12 has external threads 30 and a tip 32 at the distal end of the anchor 12 to facilitate threaded insertion into the tibia 2. At the proximal end 34 (as best shown in FIGS. 3B and 3C), the anchor has a set of slots 36 that are configured to receive projections of an implantation tool as described in further detail below. In this embodiment, the proximal end 34 of the anchor 12 has three slots 36 defined in the threads 30. Alternatively, the anchor 12 can have any number of slots 36 for use in coupling with an implantation tool. In accordance with one implementation, the slots 36 are defined in the threads 30 as shown such that the implantation tool (as described below) can couple with the anchor 12 without requiring a coupling component disposed within the lumen 38 of the anchor 12 or requiring any type of coupling component that extends proximally or radially from the anchor 12. As such, these slots 36 defined within the threads 30 allow the lumen 38 to be free to be utilized for other purposes/functions, and also minimizes the profile of the anchor 12 both radially and proximally. In a further alternative, the anchor 12 can have any coupling structure or feature at the proximal end 34 that allows for coupling with an implantation tool.

In accordance with one implementation, the first anchor 12 has threads configured the same as a standard metallic cortical or cancellous bone screw 12. In another embodiment, the implantation tool is featured to drive the screw into the bone via fingers or protrusions 146 from an annular space between the major and minor diameters of the threads and at a distance distal to the proximal aspect of the screw. This embodiment allows the anchor to engage the lateral cortical aspect of the tibia while presenting a smooth profile on the lateral bone surface and allows complete circumferential thread engagement right up to the lateral bone surface.

Figure 4:
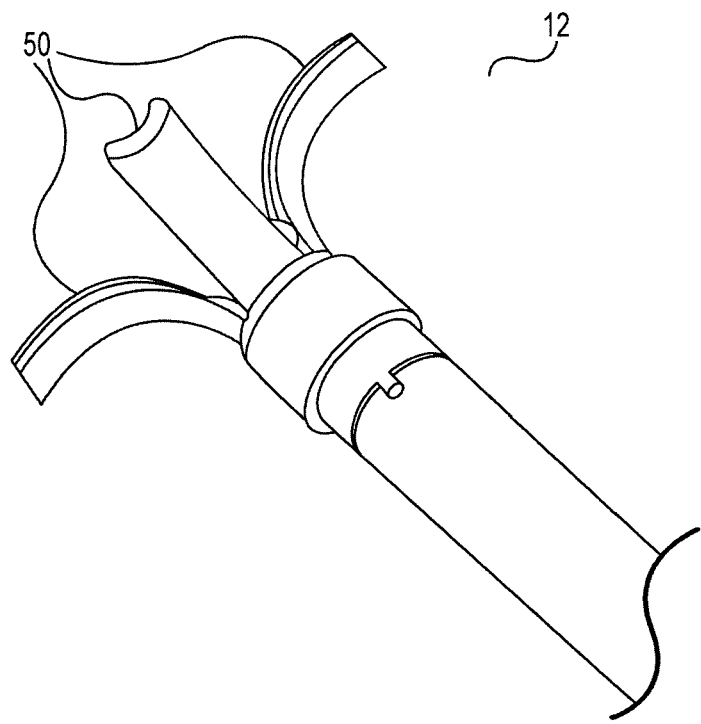
FIG. 4 is a perspective view of a distal end of a first anchor, according to another embodiment.

Alternatively, the first anchor 12 can be any known type of anchor, including, for example, a screw, an expandable anchor, or an external button. In one exemplary alternative embodiment as depicted in FIG. 4, the first anchor 12 is a pronged anchor 12. In this implementation, the anchor 12 has prongs 50 that extend out from the anchor 12 into the bone to facilitate fixation of the anchor 12 in the bone.

It is understood that certain embodiments of the first anchor 12 are substantially rigid and are configured to be capable of cutting bone (e.g. self-tapping threads). Additionally, various embodiments of the first anchor 12 can also have radiopacity or radiolucency. It is also understood that the first anchor 12 material must be biocompatible.

It is further understood that any of the first anchor embodiments contemplated herein, or portions thereof, can be made of any suitable material, including plastically deformable materials, biocompatible polymers, relatively rigid polymeric materials, or metals. Specific examples can include stainless steel, MP35N, titanium and titanium alloys, nitinol, plastic, UHMWPE, cross-linked UHMWPE, PEEK, polycarbonate, polylactic acid (PLLA or PDLA), bone allograft, hydoxyapatite coral coated for ingrowth, human dermis, porcine intestinal mucosa, fetal bovine skin, porcine skin, cadaveric fascia, marlex mesh, hernia mesh, polytetrafluorethylene, absorbable suture, or umbilical tape. According to one embodiment, a first anchor 12 having prongs is formed of commercially pure titanium.

These various characteristics and any other alternative characteristics discussed above or elsewhere with respect to various first anchor 12 embodiments can apply to any of the anchors 12 described with respect to any of the device embodiments described or contemplated herein.

Figure 5B:
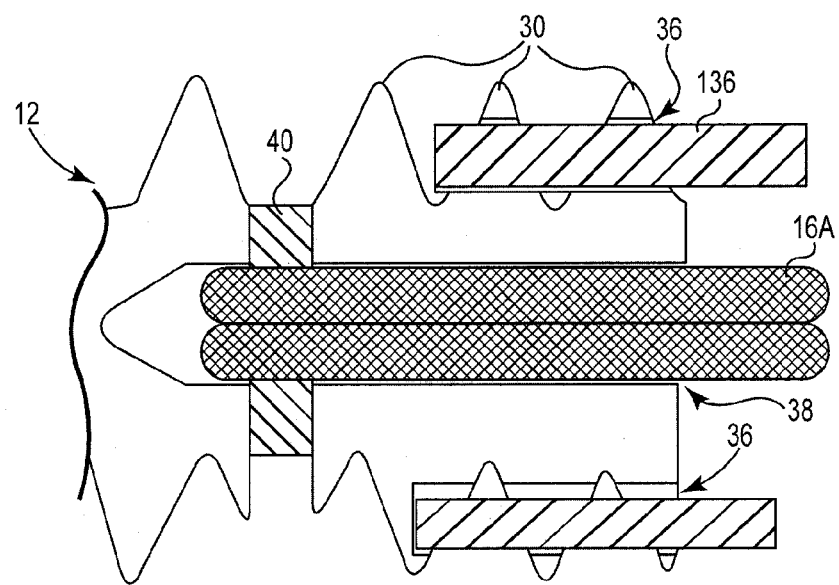
FIG. 5B is an expanded cross-sectional side view of a first anchor coupled to a flexible component and a deployment tool (also referred to herein as an "implantation tool"), according to one embodiment.
Figure 5C:
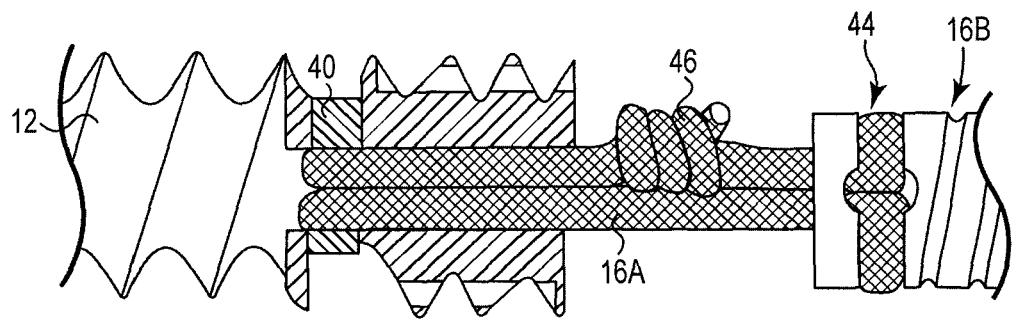
FIG. 5C is an expanded cross-sectional side view of a first anchor coupled to flexible component that is coupled to a base component, according to one embodiment.

A tether 16 in accordance with one implementation is depicted in FIGS. 5A-5D. The tether 16 has a flexible component 16A and a base component 16B. The flexible component 16A embodiment depicted in FIGS. 5B-E is a suture 16A coupled at the distal end to the first anchor 12 and at the proximal end to the base component 16B. In one embodiment as best shown in FIG. 5C, the single suture 16A is tied together at knot 46 and formed into a single loop 16A.

Figure 5D:
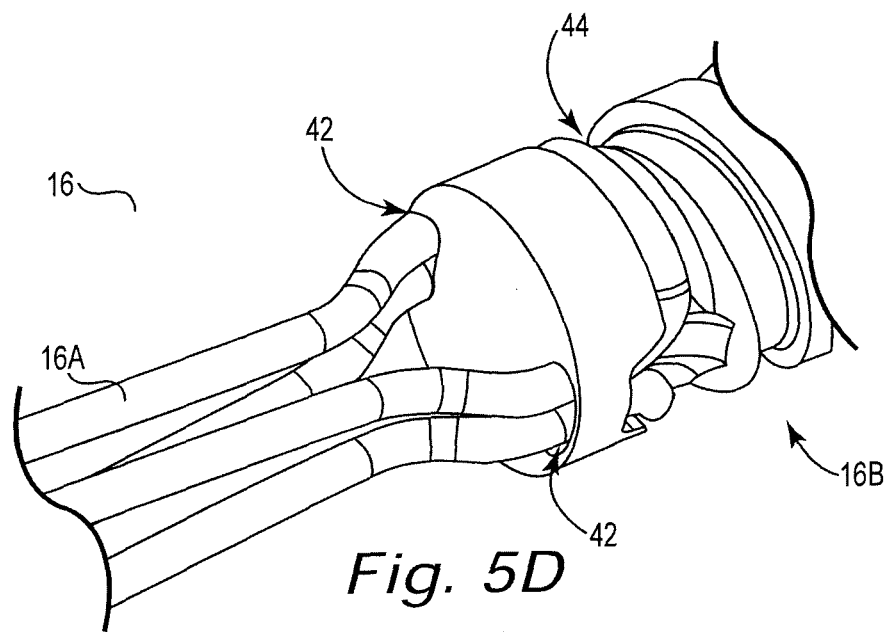
FIG. 5D is a perspective view of a flexible component coupled to a base component, according to one embodiment.
Figure 5E:
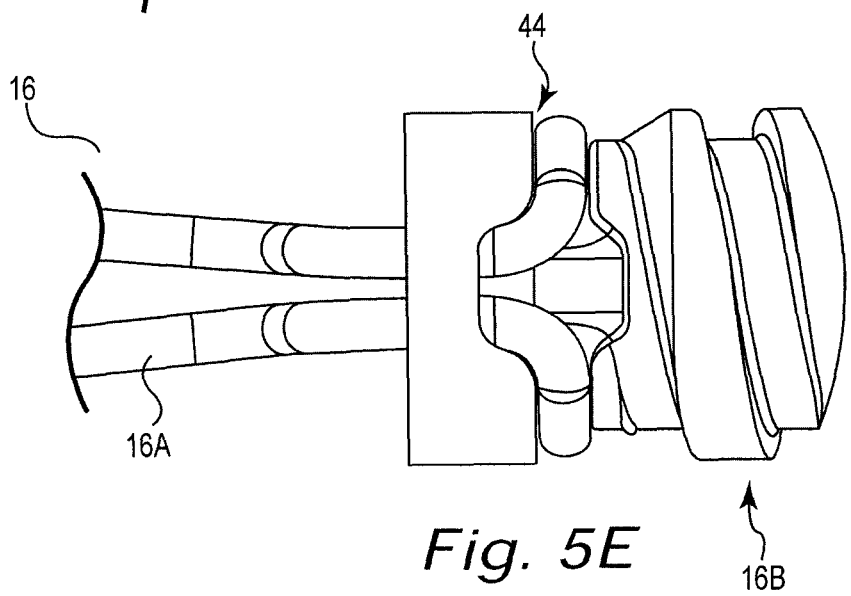
FIG. 5E is a side view of the flexible component coupled to the base component of FIG. 5D, according to one embodiment.

As best shown in FIGS. 5C, 5D, and 5E, the suture 16A comprises a single line having two loops coupled to the distal end of the base component 16B. More specifically, the loops of the suture 16A are threaded through two holes 42 at the distal end of the base component 16B and looped around a portion of the circumference of the base component 16B in a groove 44 and threaded back through the other of the two holes 42. As best shown in FIGS. 5D and 5E, the two holes 42 are directly below and orthogonal to the groove 44 in the base component 16B. In one embodiment, these holes 42 are in this location to maximize the load bearing capacity of the base component 16B. The suture 16A places a load on the base component 16B when the implant is placed in tension from natural physiologic motion. The positioning of the holes 42 as shown in FIG. 5D can maximize the capacity of the base component 16B to withstand that load. In accordance with one embodiment, the maximum load capacity of the groove 44 at the distal end of the base component 16B is 75 lbs. Alternatively, the maximum load capacity can be any amount between 0 and 75 lbs. In one implementation, the load capacity is directly proportional to the size of the cross-sectional area of the base component 16B. According to one embodiment, the distal end of the base component 16B can be configured to have a maximum load capacity with a predetermined failure point based on the materials and specific dimensions selected for the base component 16B.

As best shown in FIGS. 5B and 5C, the suture 16A also has two loops coupled to the proximal end of the first anchor 12. More specifically, the loops of the suture 16A are threaded around a cross pin 40 within the lumen 38 at the proximal end of the first anchor 12.

According to one method of making the device, the suture 16A is coupled to or threaded onto the base component 16B and then the suture 16A is tied together with the knot 46. In accordance with one alternative embodiment, the cross pin 40 can be removably positioned in one of several different holes (not shown) spaced along the interior of the lumen 38 of the first anchor 12, thereby allowing for adjustment of the positioning of the pin 40 to adjust the overall distance between the anchor 12 and the base component 16B. In addition, the adjustment capability of the pin 40 eliminates any slack in the suture 16A resulting from the need for the user to tie the suture 16A together with the knot 46.

In one embodiment, the distance between the anchor 12 and the base component 16B should range from about 0.050 inches to about 0.150 inches. Alternatively, the distance can be any amount that results in the desired positioning of the tibia 2 and fibula 4 as discussed elsewhere herein.

Alternatively, the loops of the suture 16A can be threaded around or through any type of projection or similar feature on the anchor 12. In a further alternative, the flexible component 16A can be coupled to the base component 16B and the first anchor 12 in any known fashion.

Figure 5F:
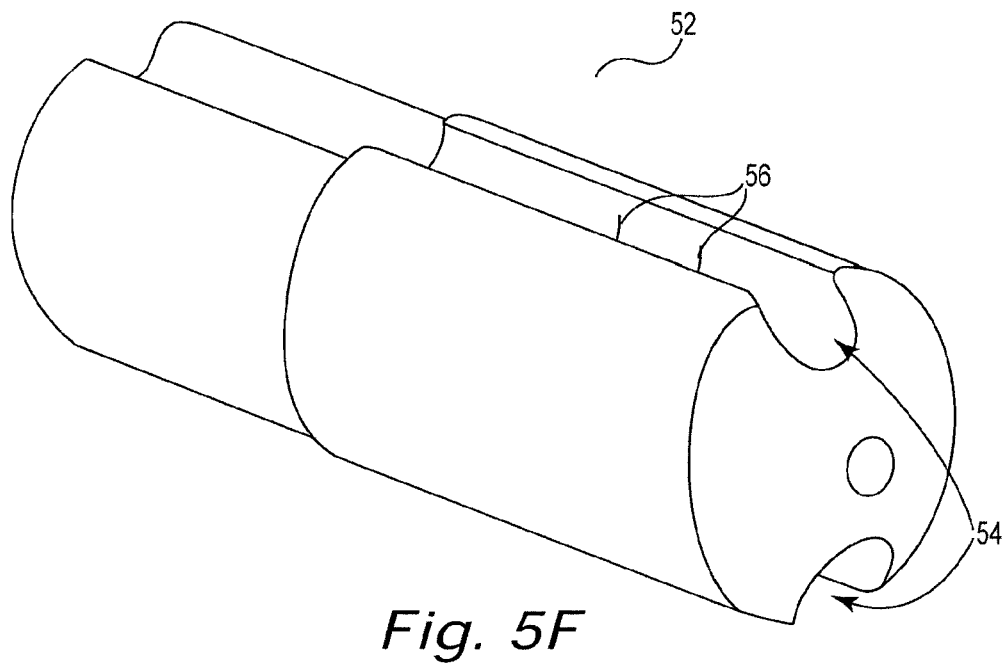
FIG. 5F is a perspective view of a plug, according to one embodiment.
Figure 5G:
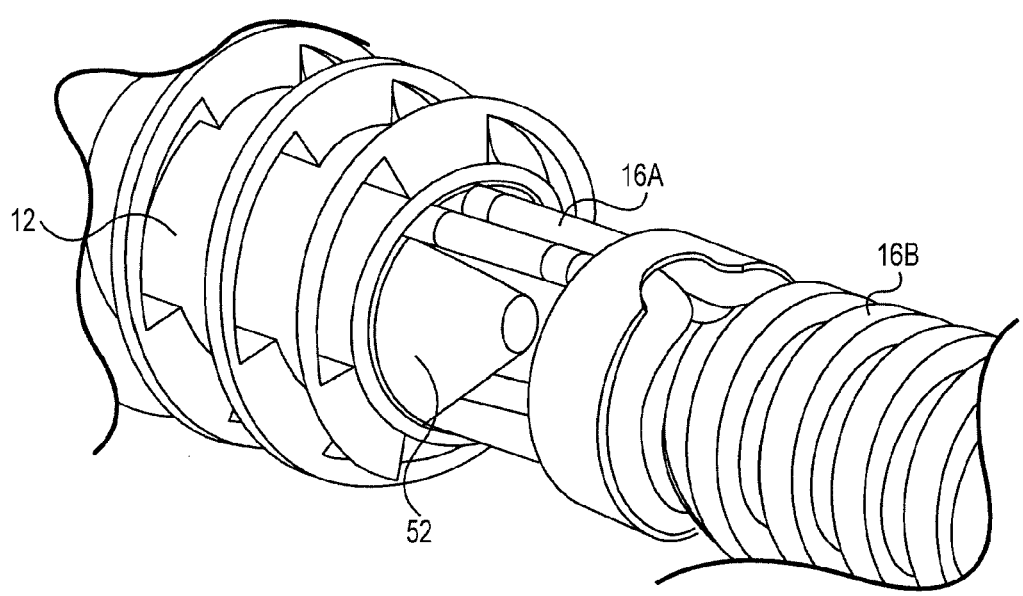
FIG. 5G is a perspective view of the plug of FIG. 5F coupled to a first anchor and a tether, according to one embodiment.

According to another alternative embodiment, the flexible component 16A can be connected to the first anchor 12 such that there is no knotting. One such embodiment is shown in FIGS. 5F and 5G, which depict a plug 52 that can be used in combination with the flexible component 16A and the first anchor 12 to attach the flexible component 16A to the first anchor 12. The plug 52 has grooves 54 defined on opposite sides of the plug 52, and the grooves 54 have projections 56 in the walls of the grooves 54. The plug 52 is configured to be positionable within the lumen 38 at the proximal end of the first anchor 12. As best shown in FIG. 5G, the flexible component 16A of the tether 16 can be coupled to the first anchor 12 by positioning the sutures 16A within the grooves 54. According to certain embodiments, the projections 56 in the grooves 54 urge the strands of the suture 16A contained therein against the internal surface of the lumen 38, thereby creating a tension or frictional fit that retains the suture 16A in place and thus results in the attachment of the suture 16A to the first anchor 12. In accordance with one implementation, this plug 52 can be used with a flexible component 16A comprising multiple sutures 16A or strands of sutures 16A. Alternatively, it can also be used with a single stranded suture 16A or any other type of suture-like flexible component 16A. In one embodiment, this implementation can allow flexibility during assembly in establishing the separation distance between the first anchor 12 and the tether 16.

According to an alternative implementation, the flexible component 16A can be a set of multiple (e.g., four) separate suture lines, each of which is individually coupled to the first anchor 12 and the tether base 16B. In a further alternative, the flexible component 16A can be one suture, two sutures, three sutures, four sutures, or more than four sutures. In yet another alternative, the flexible component 16A can be any known flexible component or material and can be coupled to the cylindrical base component 16B in any known fashion using any known coupling components or methods.

In one alternative implementation, the flexible component 16A can have a predetermined failure point such that it will fail at some predetermined amount of applied force that is lower than the anticipated anchoring force of the first anchor 12 in the tibia 2 or the second anchor 14 in the fibula 4. For example, if the expected anchoring forces of the first anchor 12 and second anchor 14 are 60 pounds, the flexible component 16A can be designed to break at a lower force, such as, for example, 50 pounds. As such, if the device is exposed to an unusually high biomechanical force, such as an unexpected fall by the patient, the flexible component 16A in this embodiment is designed to fail before the high force causes the first anchor 12 or second anchor 14 to be pulled from their respective implantation sites. Although the result is a failure of the tether 16, it is understood that it is easier to repair the failed tether 16 rather than repair the substantial damage resulting from an anchor being pulled out of the bone.

In yet another alternative, the flexible component 16A can be any number of individual pieces of a variety of suitable implantable materials. Such materials include monofilament or multi-filament structures such as yarns, braids, or weaves. In accordance with one embodiment, the tether has lateral flexibility, and as such, materials that could provide lateral flexibility include polyester (such as Dacron™), ultra-high molecular weight polyethylene (UHMWPE), high strength expanded PTFE, or polycarbonate urethane. Other materials include those exhibiting higher elasticity, such as silicone, silicone rubber, PEBA such as Pebax™, Kraton™ polymers, polyurethane, latex, or any other elastomeric materials. In certain embodiments, the flexible component 16A is made of any flexible but non-bio-absorbable material, thereby providing long-term syndesmotic joint reduction without reducing flexibility. In other implementations, the tether embodiments can be made of a bio-absorbable material such as polylactic acid, poly-L-lactic acid, PLGA, or any known bioabsorbable material such as those used in biodegradable sutures. The bio-absorbable materials can allow for short term flexibility while being absorbed over some predetermined period of time such that the tether 16 ultimately fractures in a controlled and predetermined fashion. It is understood that various combinations of the above materials are also contemplated.

As shown in FIG. 5A, the base component 16B in this embodiment has a threaded portion 68 with external threads 70 extending from the distal end of the component 16B to some point along the length of the component 16B. The threaded portion 68 is configured to engage with the threaded lumen 84 of the second anchor 14 as described in further detail below, and the non-threaded portion 72 extends proximally from the threaded portion 68. In an alternative embodiment, the distal portion of the component 16B can have any other known mechanism for engaging with the second anchor 14 instead of threads. In various embodiments, the base component 16B is substantially rigid. In further embodiments, the base component 16B is made of a material that can be trimmed or cut as described elsewhere herein. In one embodiment, the tether base component 16B is comprised of polyether ether ketone ("PEEK"). Alternatively, the component 16B can be made of any suitable biocompatible material, such as stainless steel, titanium, cobalt alloy, polyester, PTFE, nylon, HDPE, or the like. In a further implementation, the base component 16B can be made of a flexible material, thereby resulting in greater flexibility and angular rotational freedom for the overall construct. In one implementation, a base component 16B made of flexible material allows the surgeon to tailor the system flexibility to the needs of the patient, because, for example, different patients can exhibit different levels of baseline fibula rotation.

In the embodiment as shown, the base component 16B is a cylindrical base component 16B. Further, in this embodiment, the cylindrical base component 16B is also a tubular base component 16B, meaning that it has a lumen 156 defined within the component 16B, as best shown in FIG. 12E. Alternatively, the cylindrical base component 16B has no lumen. In a further alternative, the base component 16B can have any configuration that allows for use in an implantable device as contemplated herein.

In further implementations, either or both of the flexible component 16A or base component 16B can have radiopacity or radiolucency. Further, either or both of the components 16A, 16B can be made of fatigue resistance materials.

Alternatively, instead of two components 16A, 16B, the tether 16 can be a single component. In one exemplary embodiment of a single component tether 16 or a tether 16 having no flexibility portion, the tether 16 has fracture notch or point (not shown) that can be intentionally fractured by a user or physician at some desired time. In one embodiment, the fracture notch or point can be fractured by the application of controlled torsion to the lateral aspect of the implanted tether 16 by a user or physician. For example, the fracture notch or point can be fractured after a successful soft tissue healing period. Alternatively, any known fracture structure or method can be used.

In a further alternative, the tether 16 can be any known elongate device or structure for coupling two bone anchors. In one implementation, the tether can be any tether or tether material—or variations thereof—as described in U.S. application Ser. No. 12/371,354, filed on Feb. 13, 2009 and entitled "Methods and Devices for Treating Hallux Valgus;" U.S. application Ser. No. 12/567,314, filed on Sep. 25, 2009 and entitled "Methods and Devices for Treating A Structural Bone and Joint Deformity;" U.S. application Ser. No. 12/691,646, filed on Jan. 21, 2010 and entitled "Methods and Devices for Treating Hallux Valgus;" or U.S. application Ser. No. 12/793,429, filed on Jun. 3, 2010 and entitled "Methods and Devices for Treating Hallux Valgus," each of which is hereby incorporated herein by reference in its entirety.

To further achieve short term rigidity and long term flexibility, various tether embodiments contemplated herein can incorporate a combination of rigid and bio-absorbable or rigid and flexible components, wherein the various combinations can be intended to change rigidity over time or designed to fracture in a controlled fashion.

It is further understood that any tether embodiment described throughout this application can be configured according to any of the configurations or materials described above or elsewhere herein.

Figure 6A:
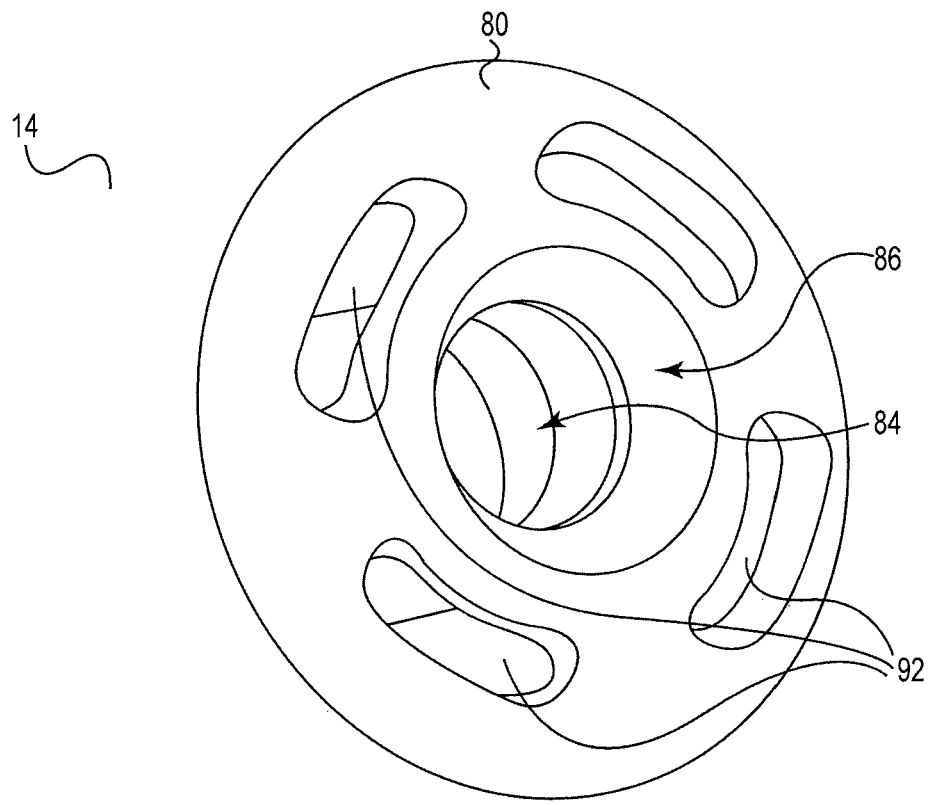
FIG. 6A is a perspective top view of a second anchor, according to one embodiment.
Figure 6B:
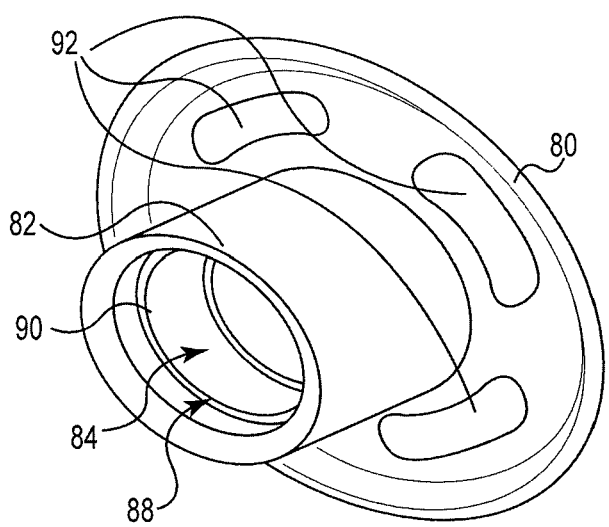
FIG. 6B is a perspective bottom view of the second anchor of FIG. 6A, according to one embodiment.

A second anchor 14 according to one embodiment is depicted in FIGS. 6A and 6B. The anchor has a head 80 at the proximal end of a body 82. The tubular body 82 has a lumen 84 defined through the length of the body 82 and through the head 80. An opening 86 to the lumen 84 is defined in the head 80 and an opening 88 to the lumen 84 is defined in the body 82. The lumen 84 has internal threads 90 configured to be threadably engageable with the external threads 70 of the tubular base component 16B of the tether 16. Alternatively, the anchor body 82 is attached to the fibula 4 by any known attachment method, material, or device, such as, for example, a porous outside surface that facilitates bony in-growth. Additionally, the body 82 can also have any known mechanism for engaging with the tether base component 16B.

In one embodiment, the second anchor 14 is configured to be positioned against or adjacent to the surface of the lateral aspect of the fibula 4, as described in further detail below. In certain alternative implementations, the anchor 14 can be configured to couple with, interface with, or otherwise be associated with a fracture fixation plate positioned against the lateral aspect of the fibula 4. Alternatively, the anchor 14 is configured to be positioned in a countersink hole or counterbore hole as described in further detail below. In yet another alternative, the anchor 14 is configured to have a low profile such that it can be positioned against the fibula without a countersink hole. For example, the anchor 14 can be thin, can have a rounded head, or can otherwise have a low profile. In a further implementation, the anchor 14 can be made of a flexible material, thereby resulting in greater flexibility and angular rotational freedom for the overall construct. In one implementation, an anchor 14 made of flexible material allows the surgeon to tailor the system flexibility to the needs of the patient, because, for example, different patients can exhibit different levels of baseline fibula rotation.

In this embodiment, the head 80 has four slots 92 defined in the head 80 that are configured to couple with a driver tool, such as the driver tool 160 discussed below, by receiving projections on the driver tool such as the driver tool 160 as described in further detail below. It is understood that, while depicted in a particular configuration in FIGS. 6A and 6B, the four slots or holes 92 can be defined in the head 80 in any known shape, configuration, or position on the head 80. Alternatively, any number of holes 92 can be defined in the head 80. In a further alternative, the second anchor 14 can have any structure or feature that can be used to couple with a driver tool. In a further alternative, the second anchor 14 can be the same as or similar to the threaded bone anchor embodiments disclosed in U.S. application Ser. No. 12/691,646 or 12/567,314, both of which are incorporated by reference above. It is understood that any of the second bone anchor embodiments contemplated herein can be made of any known material that is suitable for implantable medical components or devices. According to certain implementations, the second anchor 14 is substantially rigid. In one embodiment, the second bone anchor can be made of a relatively rigid material such as stainless steel, titanium, a rigid polymer such as PEEK, or the like. In further implementations, the anchor 14 can have radiopacity or radiolucency.

Figure 6C:
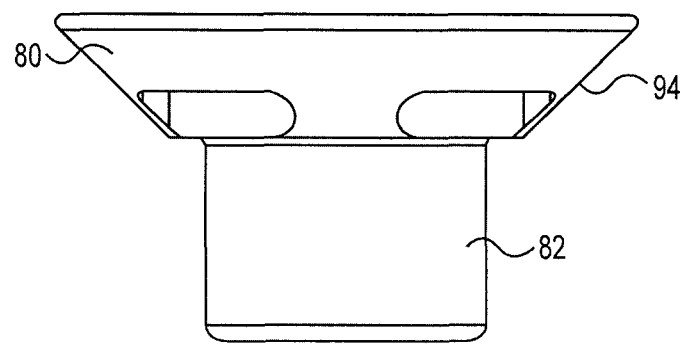
FIG. 6C is a side view of a second anchor, according to another embodiment.
Figure 6D:
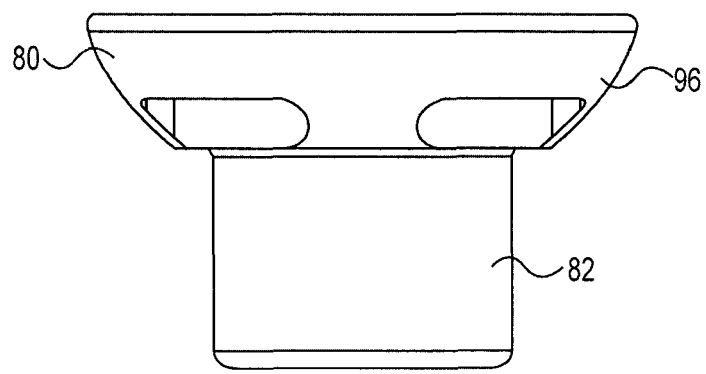
FIG. 6D is a side view of a second anchor, according to a further embodiment.
Figure 6E:
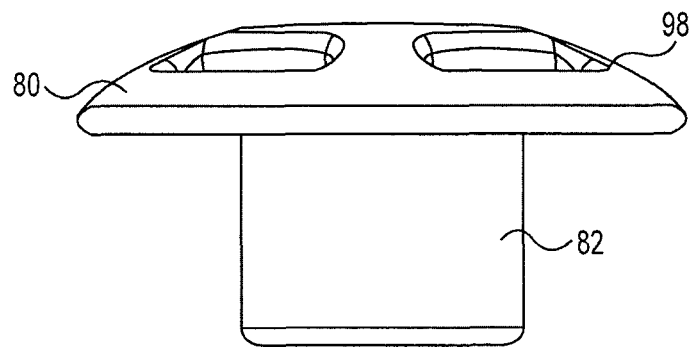
FIG. 6E is a side view of a second anchor, according to yet another embodiment.

Various alternative embodiments of the second anchor 14 are depicted in FIGS. 6C-6E. Each of these implementations has a head 80 with a different configuration. For example, the second anchor 14 embodiment in FIG. 6C has a head 80 with a substantially straight, angled wall 94 between the top of the head 80 and the body 82. This anchor 14 can be used with a countersink hole formed in the bone as described elsewhere herein, resulting in the anchor 14 having a "zero profile" (i.e., being sunk flush into the bone). That is, the angled wall 94 is configured to fit within a countersink hole. In contrast, the second anchor 14 embodiment depicted in FIG. 6D has a head 80 with a rounded wall 96 between the top of the head 80 and the body 82. This anchor 14 can be used with a standard fixation plate, which has correspondingly rounded holes configured to receive various standard screws. The third embodiment of a second anchor 14 is shown in FIG. 6E. In this implementation, the top 98 of the head 80 is rounded. The rounded head 80 has a minimal profile with an optimal footprint, and thus can be used when there is no countersink, counterbore, or fixation plate.

Various implantation methods, systems, and devices can be used to implant treatment devices similar to those depicted in FIGS. 2-6B. In accordance with one embodiment, a treatment device can be implanted in the following manner.

Figure 7:
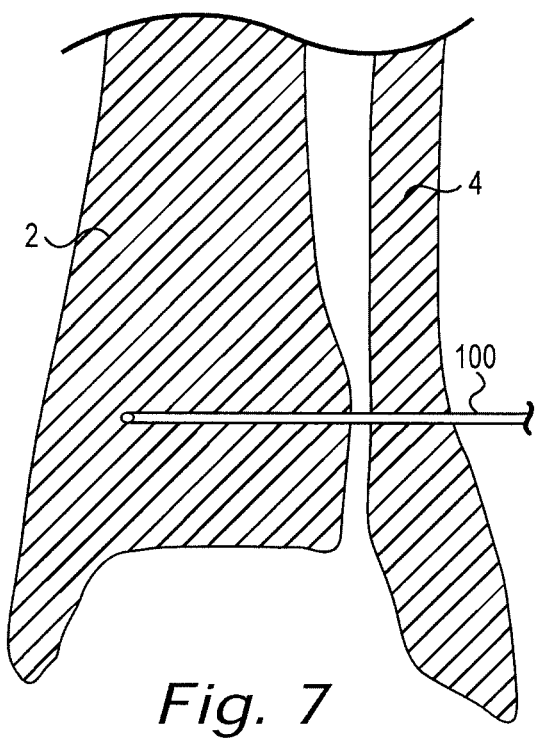
FIG. 7 is a schematic depiction of a tibia and fibula, in which a guidewire has been positioned through the fibula and into the tibia, according to one embodiment.

First, as shown in FIG. 7, a guidewire 100 is inserted through the fibula 4 and into the tibia 2. In one embodiment, the guidewire 100 is 304 Stainless Steel, which is commercially available from Orthomed. In certain embodiments, the guidewire 100 can also be known as a "K-wire."

Figure 8A:
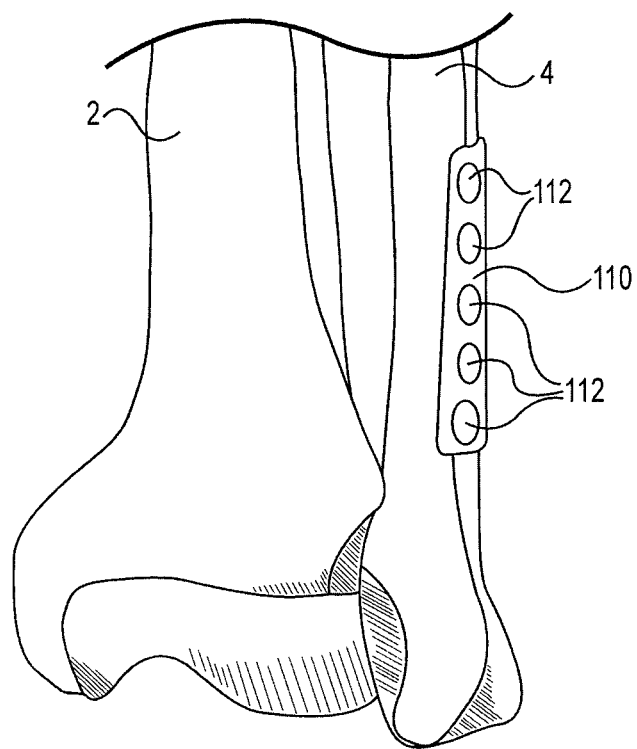
FIG. 8A is a schematic depiction of a tibia and fibula, in which a fixation plate has been positioned on the fibula, according to one embodiment.

The guidewire can be positioned in the bones 2, 4 using any known procedure. Alternatively, the procedure set forth in FIGS. 8A-8D can be used, especially in those situations in which the fibula 4 has been fractured. First, as shown in FIG. 8A, a plate 110 is positioned along the fibula 4 at the point of fracture. The plate 110 according to one implementation has multiple holes 112 defined through the plate 110.

Figure 8B:
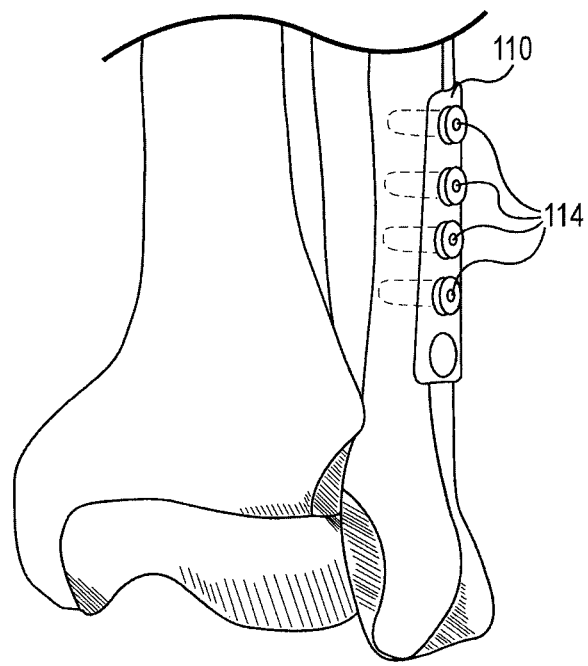
FIG. 8B is a schematic depiction of the tibia and fibula of FIG. 8A, in which screws have been positioned through the fixation plate, according to one embodiment.

Once the plate 110 is positioned correctly/as desired, one or more bone anchors or screws 114 are inserted through one or more of the holes 112 and embedded into the bone 4, as shown in FIG. 8B. In this embodiment, four anchors 114 are inserted through four holes 112. Alternatively, any number of any known type of fixation components can be used. These anchors 114 secure the plate 110 against the bone 4 and thereby stabilize the fracture.

Figure 8C:
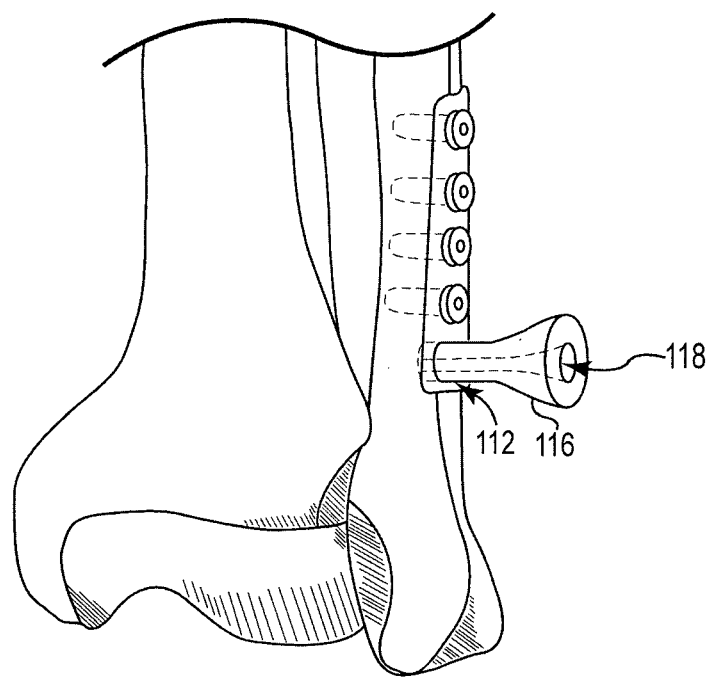
FIG. 8C is a schematic depiction of the tibia and fibula of FIG. 8A, in which a wire guide has been positioned into the fixation plate, according to one embodiment.
Figure 8D:
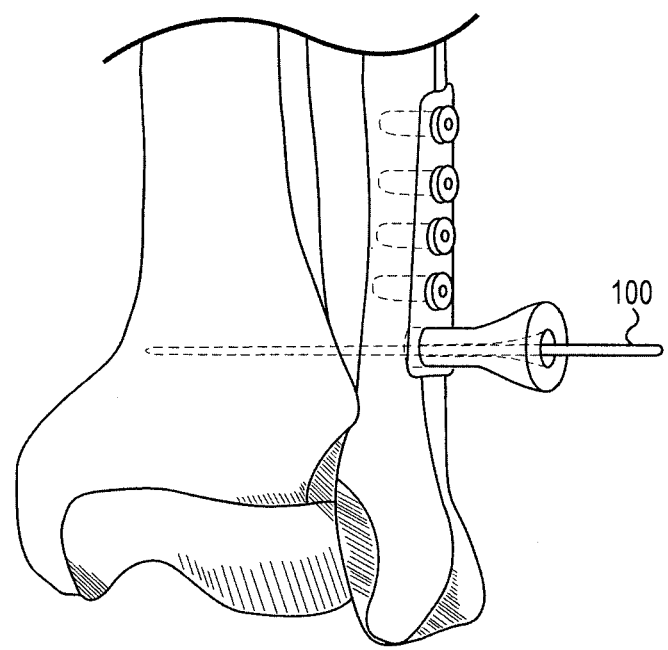
FIG. 8D is a schematic depiction of the tibia and fibula of FIG. 8A, in which guidewire has been positioned through the fixation plate and into the bones, according to one embodiment.

Once the plate 110 is secured, a wire guide 116 can be inserted into the remaining hole 112, as shown in FIG. 8C. The wire guide 116 is any known guide for guiding insertion of a guidewire (such as, for example, a K wire or any other known guidewire) through the guide 116 and the plate 110 and into the bone 4. The wire guide 116 has a lumen 118 defined through the length of the guide 116 that is configured to receive the guidewire.

When the wire guide 116 is in place, the guidewire 100 is inserted through the lumen 118 in the wire guide 116 and into the bone 4. In one embodiment, the guidewire 100 is inserted through the fibula 4 and into the tibia 2.

Figure 9:
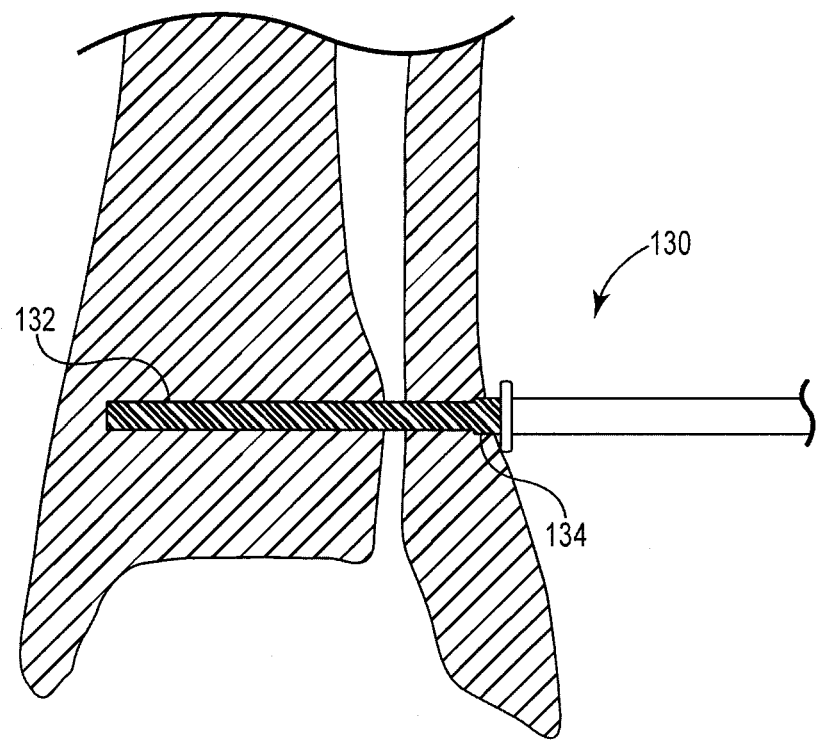
FIG. 9 is a schematic depiction of a drill positioned in a tibia and fibula, according to one embodiment.
Figure 10:
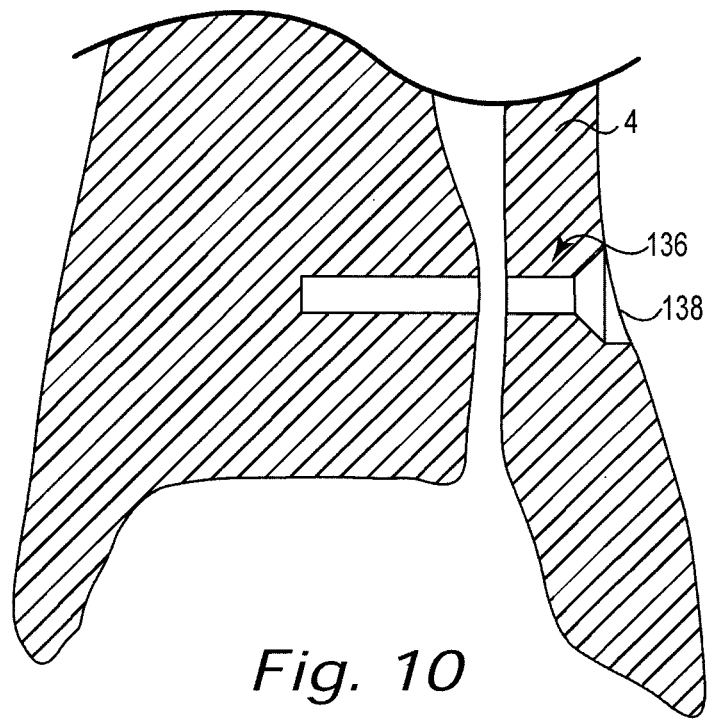
FIG. 10 is a schematic depiction of a hole created by a drill in a tibia and fibula, according to one embodiment.

Referring again to implantation steps when a plate 110 is not utilized, once the guidewire is in place, as shown in FIG. 9, a drill 130 having a lumen (not shown) defined through the length of the drill 130 is positioned over the guidewire 100 and used to drill a hole through the fibula 4 and into the tibia 2, using the guidewire 100 as a guide. The drill 130 has a drill bit 132 that has a countersink component 134 at the proximal end of the bit 132. The countersink component 134 is a portion of the drill bit 132 having a larger diameter than the rest of the bit 132, thereby being able to form a countersink hole portion near the surface of the fibula bone 4 that is wider than the rest of the hole. One example of the resulting hole 136 with the countersink hole 138 at or near the surface of the bone 4 is depicted in FIG. 10. The countersink hole 138 allows the second anchor 14 to be countersunk into the bone 4 as subsequently depicted in FIGS. 20-22. Alternatively, the drill bit 132 has a counterbore component that forms a counterbore hole at or near the surface of the bone, wherein the counterbore has flat sides instead of the angled sides of a countersink hole.

Figure 11:
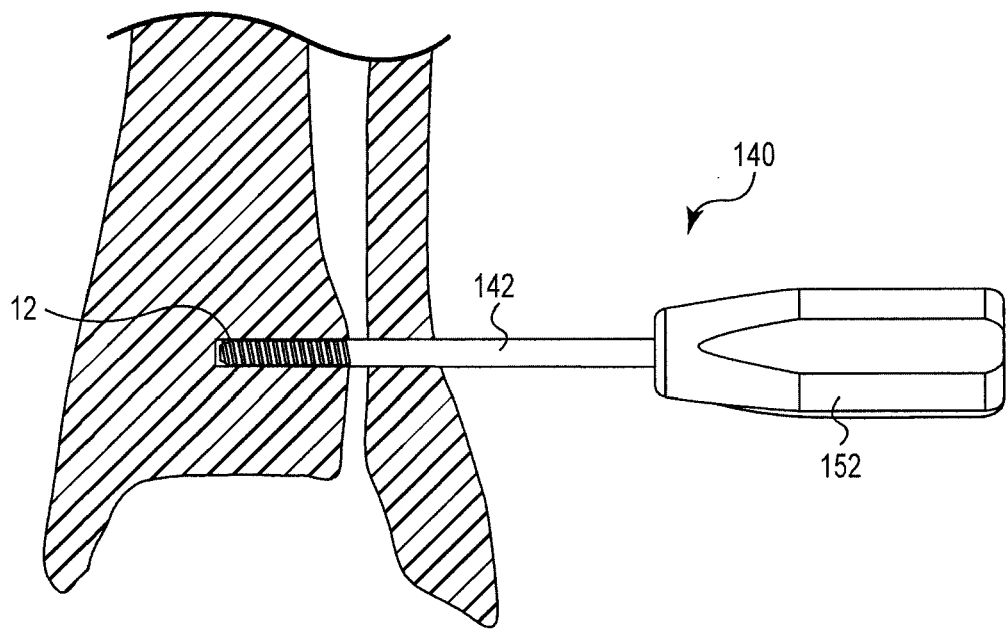
FIG. 11 is a schematic depiction of a deployment tool and first anchor being positioned into a tibia and fibula, according to one embodiment.

Once the hole 136 has been drilled, an implantation tool 140 (also referred to herein as a "deployment tool") is used to position the first anchor 12 and the tether 16 in the tibia 2 and the fibula 4. That is, as shown in FIG. 11, the tool 140 with the first anchor 12 attached to the distal end of the tool 140 is inserted into the hole 136 such that the first anchor 12 is positioned in the tibia 2. In one embodiment, the hole in the tibia 2 has a diameter that is less than the diameter of the threads 30 on the first anchor 12, thereby requiring that the first anchor 12 be urged into the hole 136 in the tibia 2 by rotating the tool 140 and thereby rotating the first anchor 12 and urging it into the hole 136.

Figure 12A:
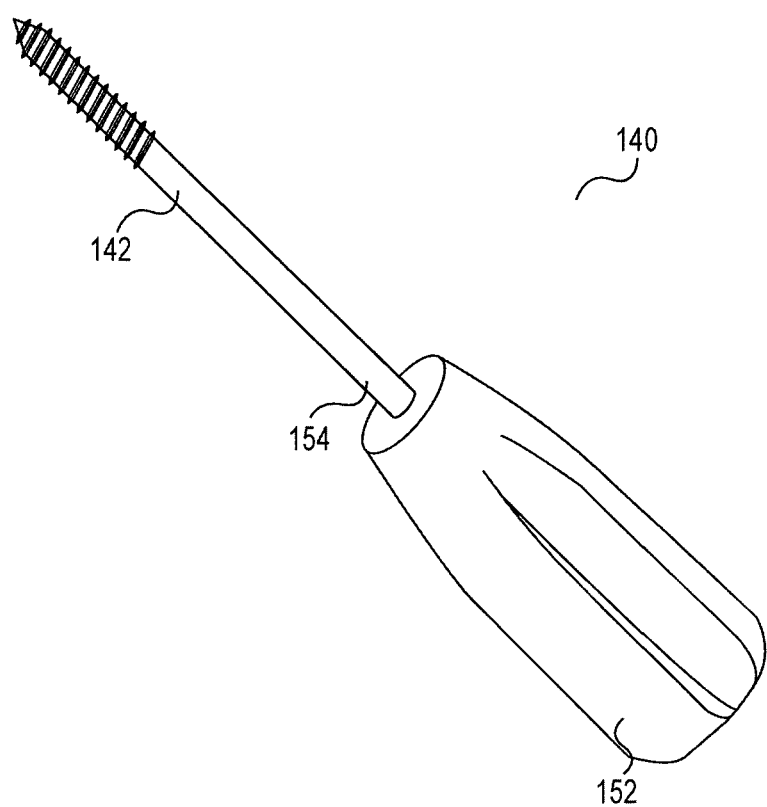
FIG. 12A is a perspective view of a deployment tool and first anchor, according to one embodiment.
Figure 12B:
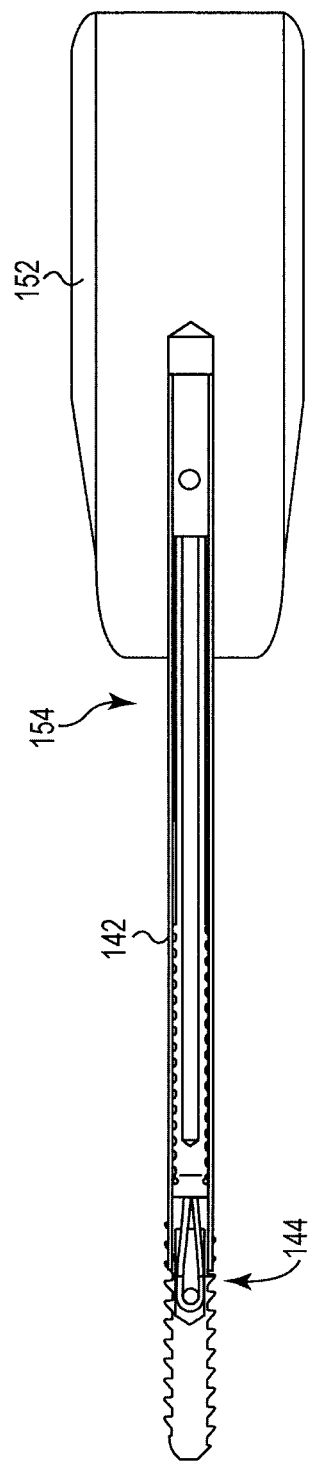
FIG. 12B is a cross-sectional side view of the deployment tool and first anchor of FIG. 12A, according to one embodiment.
Figure 12C:
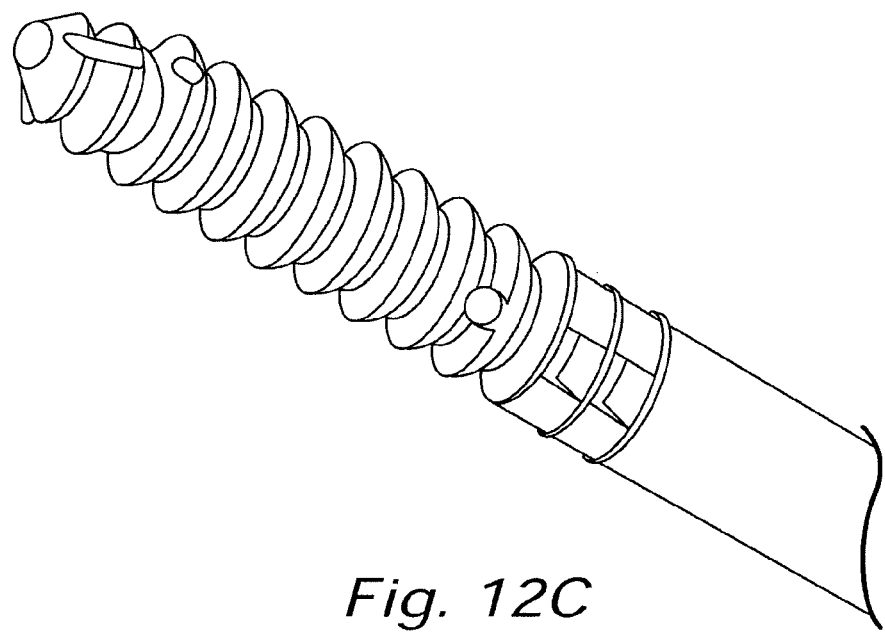
FIG. 12C is a perspective view of the distal end of the deployment tool and first anchor of FIG. 12A, according to one embodiment.
Figure 12D:
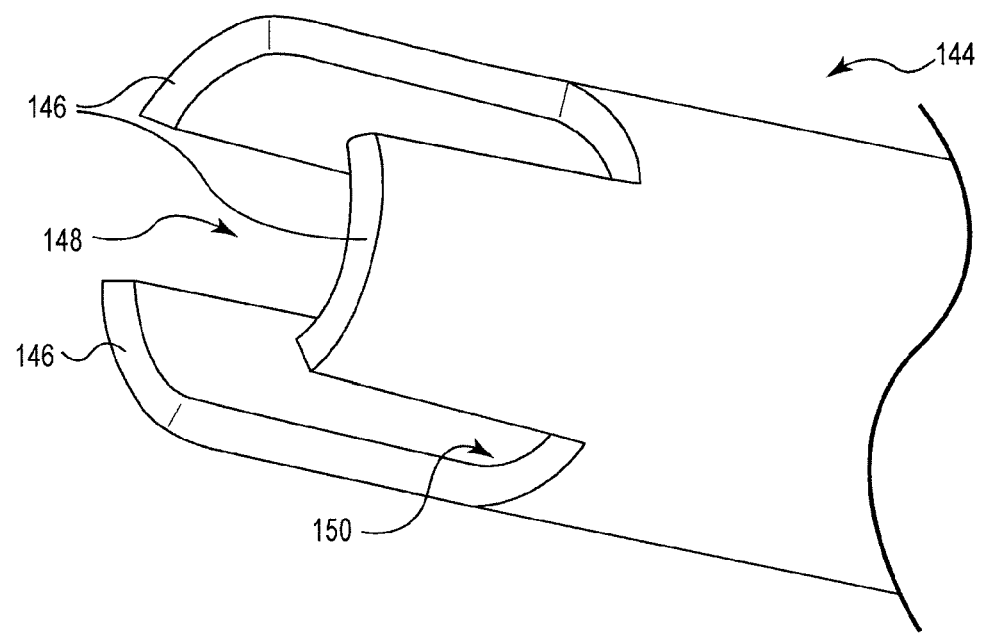
FIG. 12D is a perspective view of the distal end of the deployment tool of FIG. 12A, according to one embodiment.
Figure 12E:
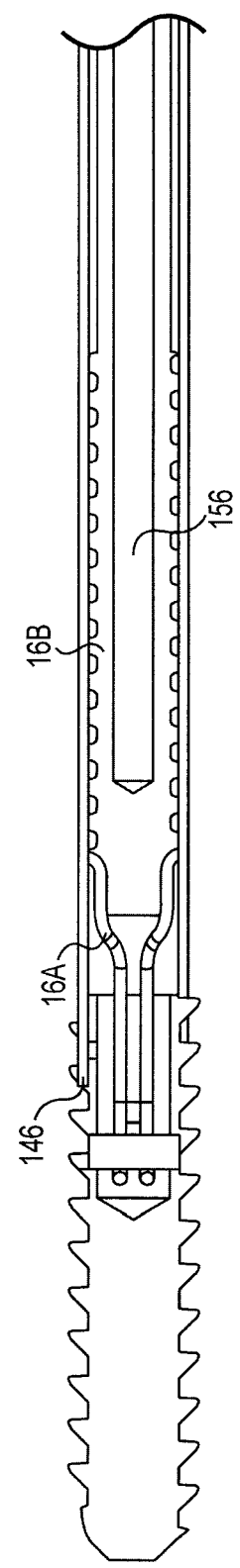
FIG. 12E is a cross-sectional side view of the distal end of the deployment tool and first anchor of FIG. 12A, according to one embodiment.

The implantation tool 140, according to one embodiment, is depicted in further detail in FIGS. 12A-F. The tool 140 has a tool body 142 with a distal end 144 having three prongs 146 as best shown in FIG. 12D. The distal end 144 with the three prongs 146 further defines an opening 148 in fluid communication with a lumen 150 that is defined within the tool body 142 and runs along the entire length of the tool body 142. The tool 140 also has a handle 152 coupled at the proximal end 154 of the tool body 142. In certain embodiments, the tool 140 is a substantially rigid tool having the ability to transmit torque to the anchor 12. For example, the tool body 142 can be made of stainless steel or any other known material for use in a driving tool for implantable medical devices. In a further example, the handle 152 can be made of polycarbonate or any other known material for use in a driving tool for implantable medical devices.

As mentioned above, prior to implantation, the distal end 144 of the tool body 142 is coupled to the proximal end 34 of the first anchor 12 as best shown in FIGS. 12A-12C. That is, the three prongs 146 are configured to be engageable with the slots 36 defined in the proximal end of the anchor 12. The slots 36 are described in further detail above with respect to FIGS. 3A-3C. FIGS. 12A-12C depict the tool 140 coupled to the anchor 12.

Figure 12F:
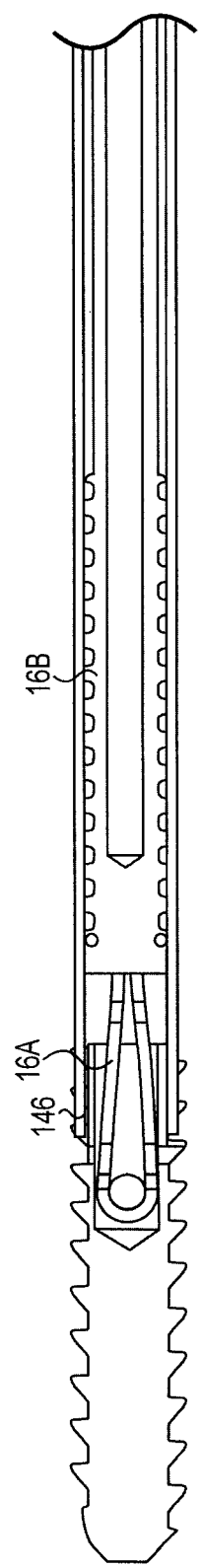
FIG. 12F is another cross-sectional side view of the distal end of the deployment tool and first anchor of FIG. 12A, according to one embodiment.

As best shown in FIGS. 12B, 12E, and 12F, prior to implantation, the tool 140 also contains the tether 16. That is, prior to implantation, the tether 16 is disposed within the lumen 150 of the tool body 142 and coupled to the first anchor 12. The flexible component 16A in this embodiment consists of a suture 16A that is coupled at a distal end to the first anchor 12 and at a proximal end to the tubular base component 16B as described in detail above. The tubular base component 16B is disposed within the lumen 150 of the tool body 142.

Figure 13:
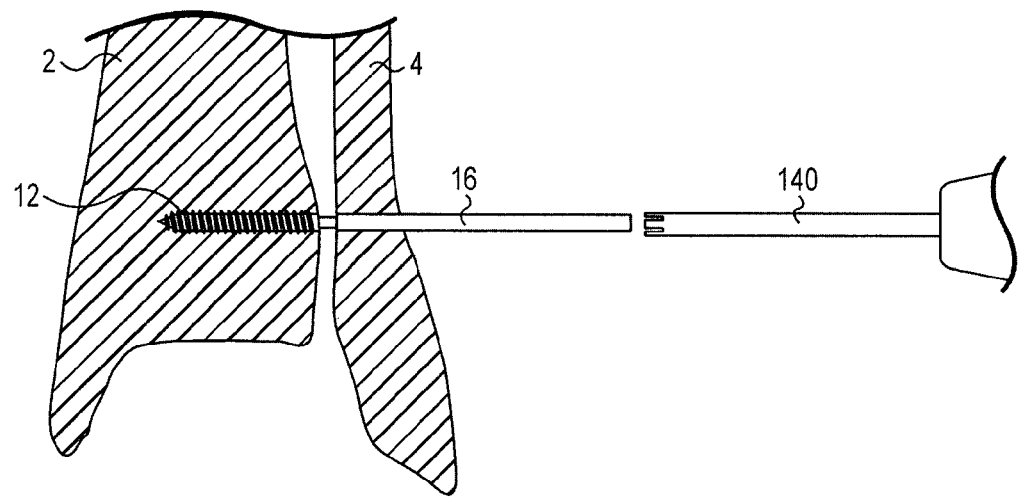
FIG. 13 is a schematic depiction of a deployment tool being removed after positioning a first anchor and tether in a tibia and fibula, according to one embodiment.
Figure 14:
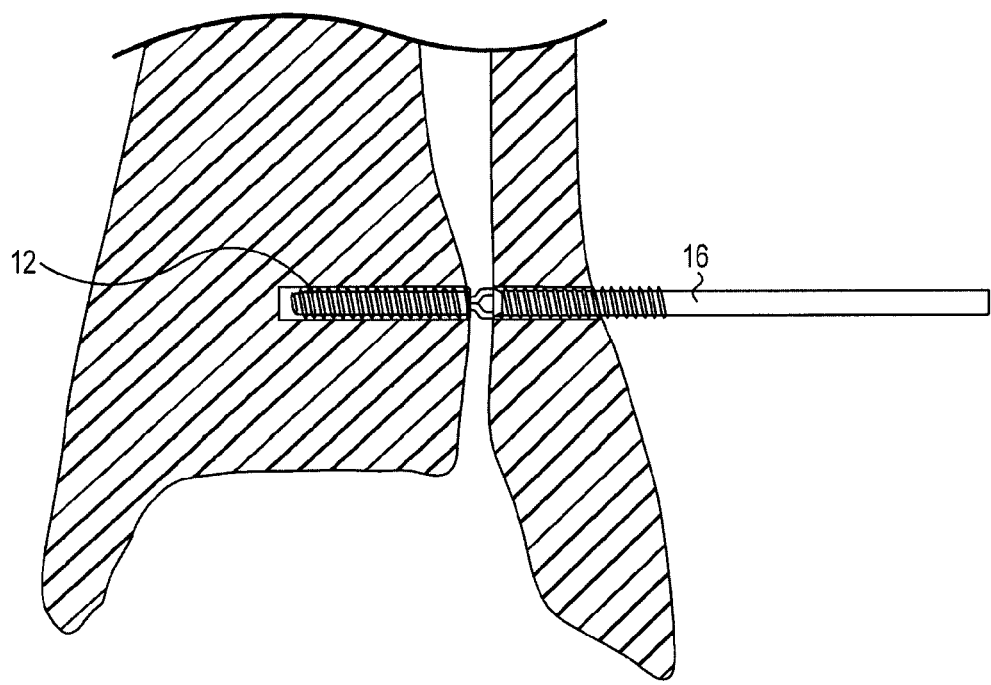
FIG. 14 is a schematic depiction of a first anchor and tether positioned in a tibia and fibula, according to one embodiment.

Upon placement of the first anchor 12 to the desired depth in the tibia 2 as discussed above (such as, for example, the proximal end of the anchor 12 being flush or substantially flush with the surface of the tibia 2 with the threads of the anchor 12 engaging the cortex), the implantation tool 140 is retracted as shown in FIG. 13, leaving the first anchor 12 implanted in the tibia 2 and the tether 16 coupled to the first anchor 12 and disposed through the hole in the fibula 4 as best shown in FIG. 14.

Once the implantation tool 140 is retracted, the second anchor 14 can be positioned over and attached to the tether 16. The second anchor 14 is depicted in FIGS. 6A and 6B and described in detail above.

Figure 15A:
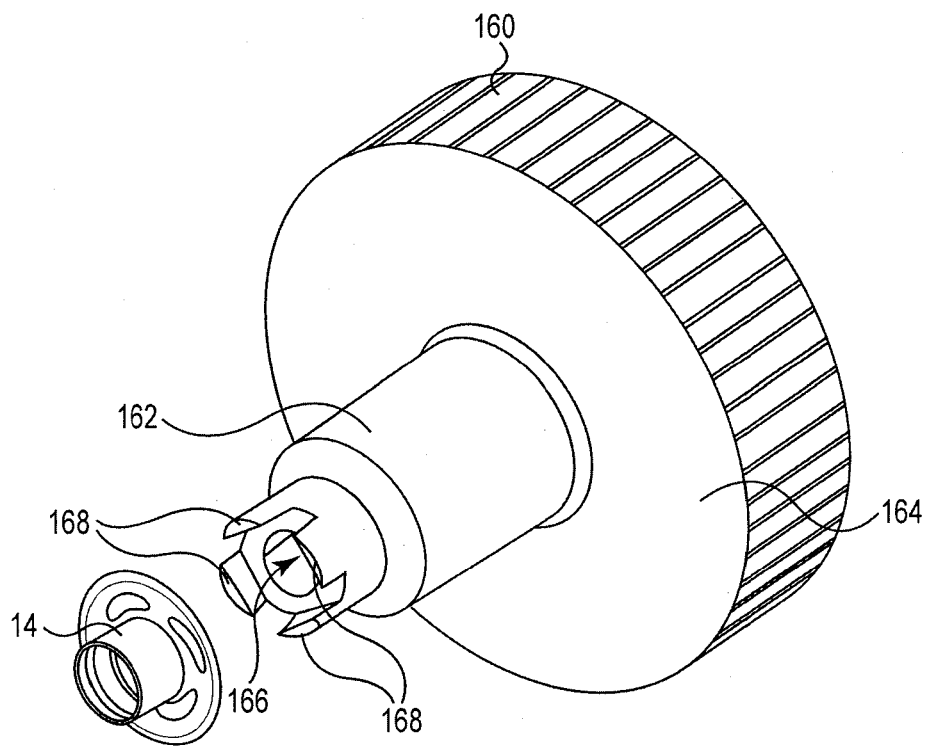
FIG. 15A is a perspective view of a driver tool, according to one embodiment.
Figure 15B:
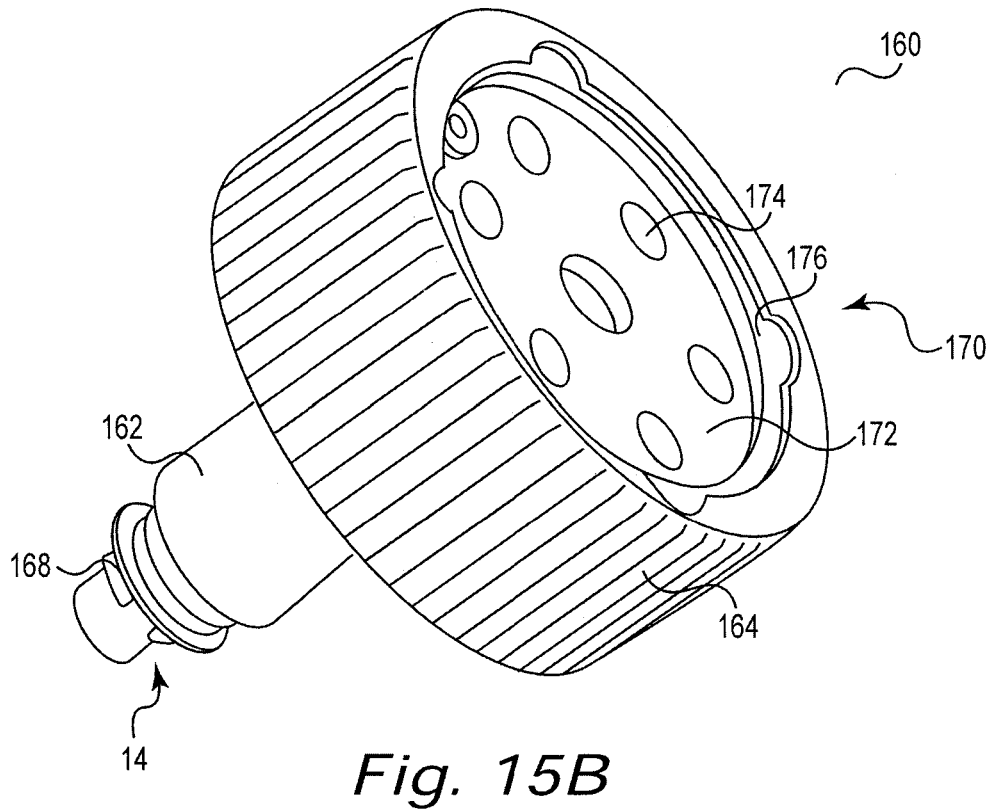
FIG. 15B is another perspective view of the driver tool of FIG. 15A, according to another embodiment.

In one embodiment, the second anchor 14 can be coupled to the tether 16 using a driver tool 160 as shown in FIGS. 15A-15B. In this implementation, the driver tool 160 has a tubular body 162 and a head 164, along with a lumen 166 defined through the length of the body 162 and through the head 164. The distal end of the body 162 has four prongs 168 configured to be engageable with the anchor 14. In certain embodiments, the tool 160 is a substantially rigid tool having the ability to transmit torque to the anchor 14. For example, the tool 160 can be made of stainless steel, polycarbonate, or any other known material for use in a driving tool for implantable medical devices. In an alternative implementation, the driver tool 160 incorporates an internal clutch 170 to assist in safe and desired placement of the anchor 14. The internal clutch 170 is comprised of a clutch plate 172, an adjustable spring (or springs, as shown) 174 and a retainer clip 176. The clutch 170 pressure is affected by the adjustable spring(s) 174. As the clutch pressure increases, the clutch plate 172 allows the surgeon to place more torque on the anchor 14 before the clutch "slips" and prohibits further increases in torque.

Figure 16A:
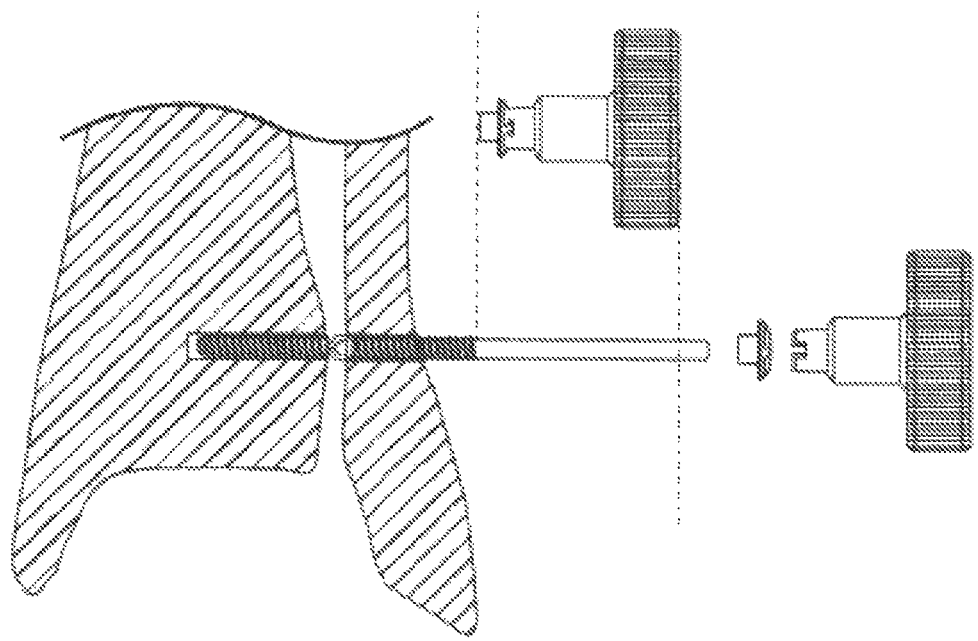
FIG. 16A is a schematic depiction of a first anchor and tether positioned in a tibia and fibula with a second anchor and driver tool prior to positioning of the second anchor onto the tether, according to one embodiment.
Figure 16B:
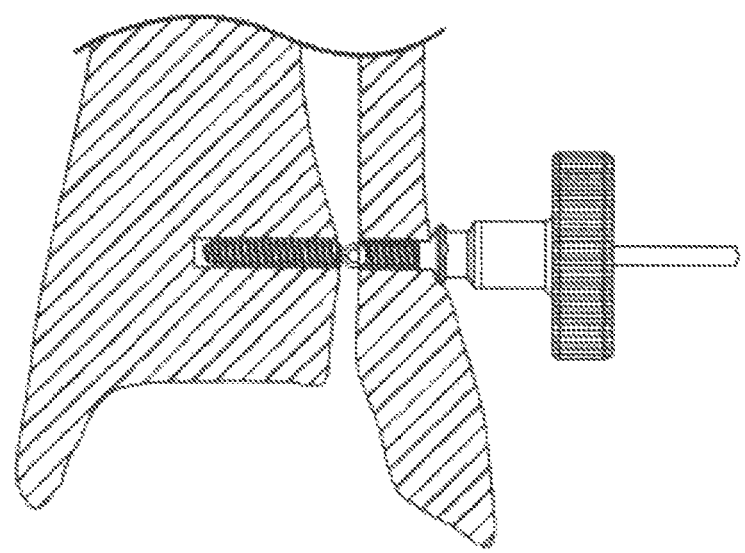
FIG. 16B is a schematic depiction of the first anchor and tether positioned in the tibia and fibula of FIG. 16A with the second anchor and driver tool positioned on the tether, according to one embodiment.

In use, the driver tool 160 is engaged with the second anchor 14 by inserting the prongs 168 into the holes 92 defined in the head 80 of the anchor 14. The anchor 14 and tool 160 are then inserted over the tubular base component 16B of the tether as best shown in FIGS. 16A and 16B. As the anchor 14 is advanced distally along the base component 16B, the anchor 14 eventually reaches the threads 70 on the base component 16B. According to one embodiment, the external diameter of the threads 70 on the base component 16B and the diameter of the internal threads 90 in the lumen 84 of the anchor are sized such that the threads 90 in the lumen 84 are engageable with the threads 70 on the base component 16B. As such, when the anchor 14 comes into contact with the threads 70 on the base component 16B, the user must start rotating the head 164 of the driver tool 160 to continue to advance the anchor 14 distally along the base component 16B. The anchor 14 is advanced until it reaches the desirable position with respect to the fibula 4. In one implementation, the anchor 14 is in the desired position when it is in contact with the fibula 4 and has urged the fibula 4 to the desired position with respect to the tibia 2, thereby treating the syndesmosis injury. One advantage of this embodiment is the ability to adjustably position the fibula 4 with respect to the tibia 2 to any desired position.

In one implementation, the "desired position" of the fibula 4 with respect to the tibia 2 is clinically measured by the medial clear space and the overlap of the tibia and fibula. According to one embodiment, this measurement can be accomplished by viewing the positions of the tibia 2 and fibula with any known technology for viewing bones in a patient. In one specific exemplary implementation, the positions of the bones can be analyzed using radiography. For example, an anterior-posterior or mortise view can be captured using radiographic equipment. It is understood that, according to one embodiment, the medial clear space on an anterior-posterior radiograph should be less than 5 mm and the overlap of the tibia and fibula should be less than 1 mm on the mortise view radiograph, as disclosed in Cottom, et al., "Treatment of Syndesmotic Disruptions with the Arthrex Tightrope: A Report of 25 Cases," *Foot and Ankle International*, Vol. 29, No. 8, pp. 773-780 (2008), which is hereby incorporated herein by reference in its entirety.

In an alternative embodiment, the "desired position" of the fibula 4 with respect to the tibia 2 can be determined by evaluating ankle function. That is, a surgeon can use ankle function as a proxy for appropriate "bony relationships" such as the relative positions of the tibia 2 and fibula 4. One such evaluation method is described in Peter, et al., "Biomechanical Effects of Internal Fixation of the Distal Tibiofibular Syndesmotic Joint: Comparison of Two Fixation Techniques," *Journal of Orthopedic Trauma*, Vol. 8, No. 3, pp. 215-219 (1994), which is hereby incorporated herein by reference in its entirety.

As such, in accordance with various embodiments, a surgeon or physician or other appropriate caregiver can initially position the second anchor 14 as described above, evaluate the relative position of the fibula 4 with respect to the tibia 2, and then re-position the anchor 14 to achieve the desired positioning.

Figure 17:
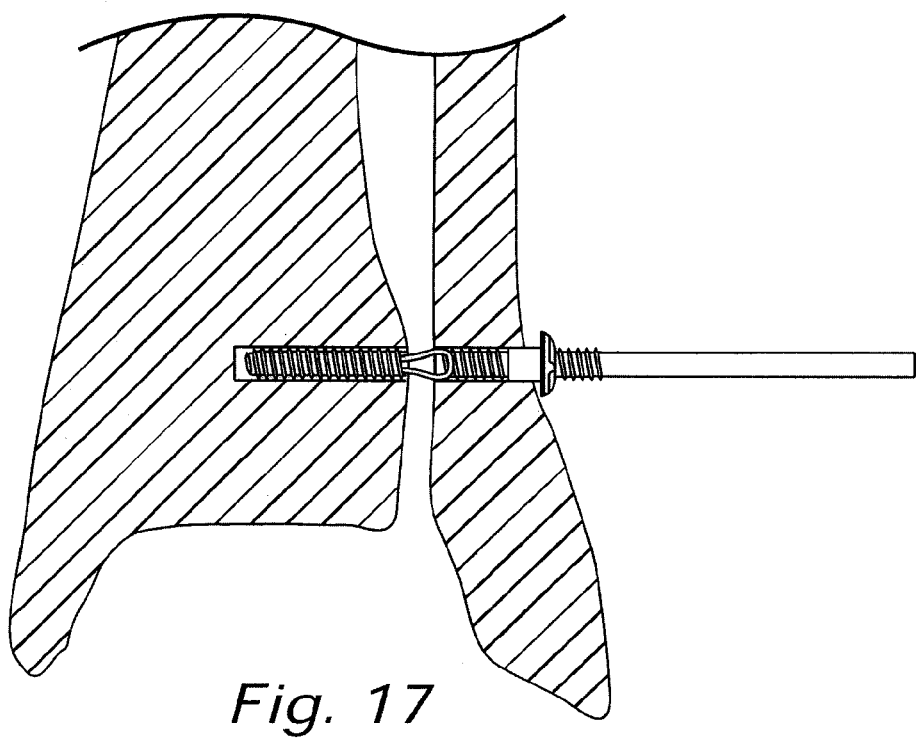
FIG. 17 is a schematic depiction of the first anchor, tether, and second anchor implanted in the tibia and fibula of FIG. 16A prior to removal of the excess tether, according to one embodiment.

Once the anchor 14 has been positioned as desired, the driver tool 160 is removed, as best shown in FIG. 17. Upon removal of the tool 160, a portion of the base component 16B extends proximally from the anchor 14. According to one embodiment, the portion of the component 16B extending proximally from the anchor 14 can be removed.

Figure 18:
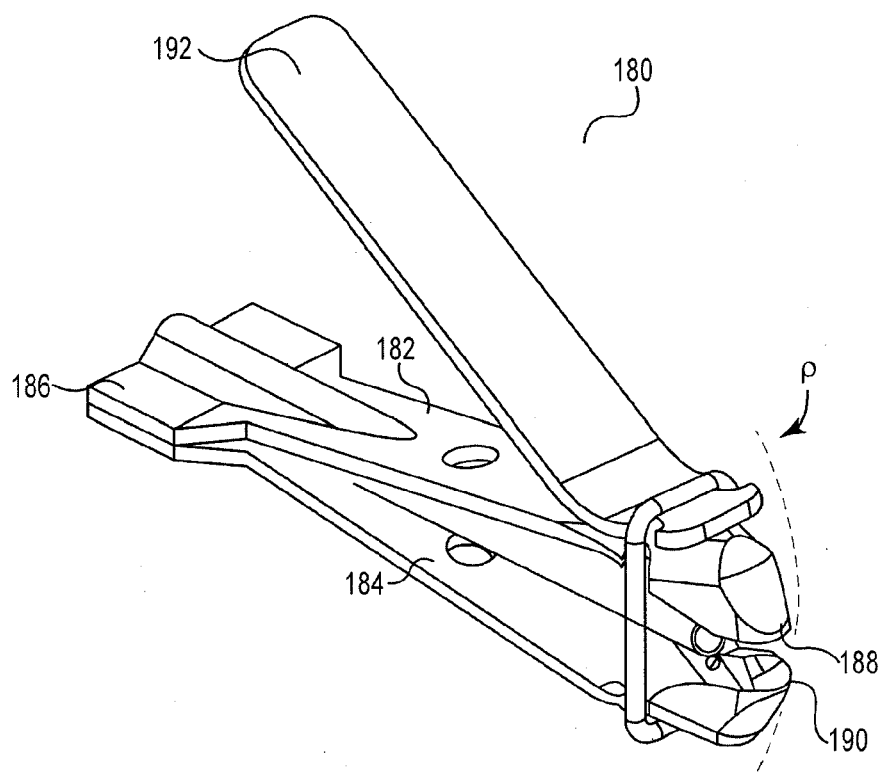
FIG. 18 is a perspective view of a cutting tool, according to one embodiment.

FIG. 18 depicts one implementation of a cutting tool 180 for removing the portion of the base component 16B extending proximally from the anchor 14. As shown in FIG. 18, the cutting tool 180 has a first arm 182 and a second arm 184 that are coupled to each other at the proximal end 186 and each have a rounded cutting edge 188, 190 at their distal ends. Alternatively, it is understood that the cutting surfaces 188, 190 of the tool 180 can take any form that allow for cutting the tether. The tool 180 also has an actuation arm 192 that is operably coupled to the first arm 182. The two arms 182, 184 are moveable in relation to each other by actuating the actuation arm 192, thereby causing the two cutting edges 188, 190 to move in relation to each other in an arcuate path as shown with reference letter "P."

In use, the tool 180 can be used to sever or otherwise remove the excess tether at a desired point such that the tether 16 does not extend beyond the proximal end of the second anchor 14. When the actuation arm 192 is actuated downward (in relation to the device 180, the two cutting surfaces 188, 190 move toward each other in the arcuate path P as described above. According to one embodiment, the arcuate path P combined with the rounded cutting surfaces 188, 190 enable the cut surface of the base component 16B to be at the outer surface of anchor 14 or at some point that is positioned within the hole in the bone (rather than external to the bone such that the tether 16B is projecting from the bone). Alternatively, any known cutting device or system can be used.

Figure 19:
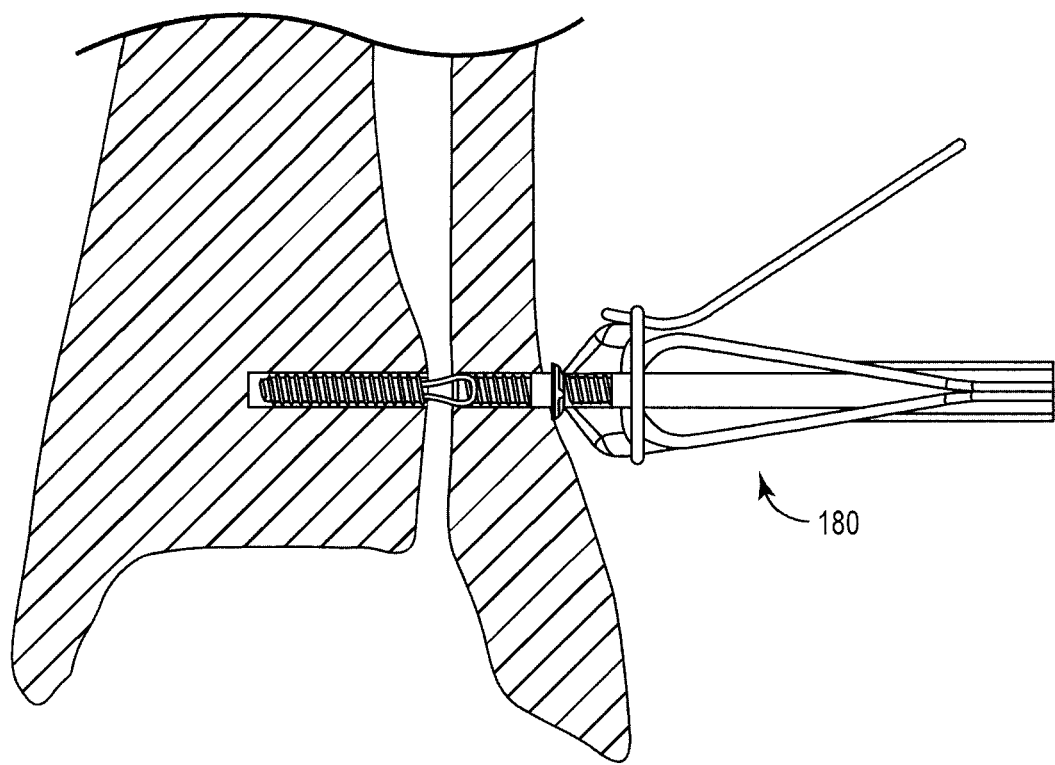
FIG. 19 is a schematic depiction of the first anchor, tether, and second anchor implanted in the tibia and fibula of FIG. 16A with a cutting tool positioned over the excess tether, according to one embodiment.
Figure 20:
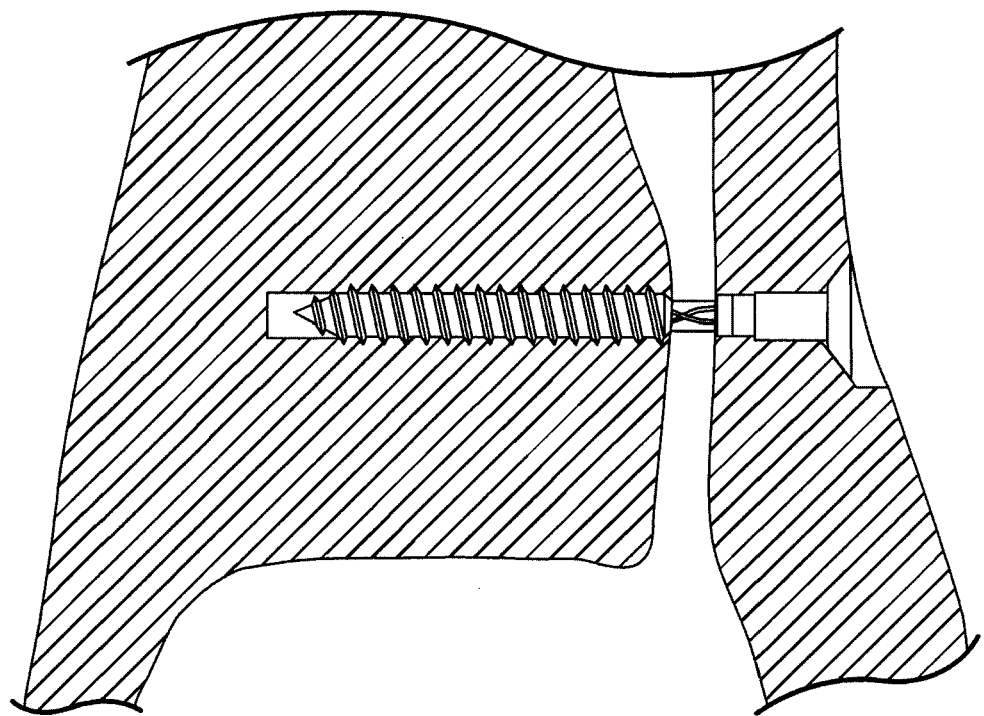
FIG. 20 is a schematic depiction of an implantable syndesmosis injury treatment device implanted in a patient, according to one embodiment.

In use, as shown in FIG. 19, the cutting tool 180 can be positioned over the base component 16B by moving the tool 180 distally over the component 16B until the tool 180 is adjacent to or in contact with the anchor 14. One the tool 180 is positioned as desired, the tool 180 can be actuated to cut the base component 16B, thereby resulting in an implanted device 10 as best shown in FIG. 20. In one implementation, the base component 16B embodiment having a lumen 156 is easier to cut than an embodiment without a lumen.

Figure 21:
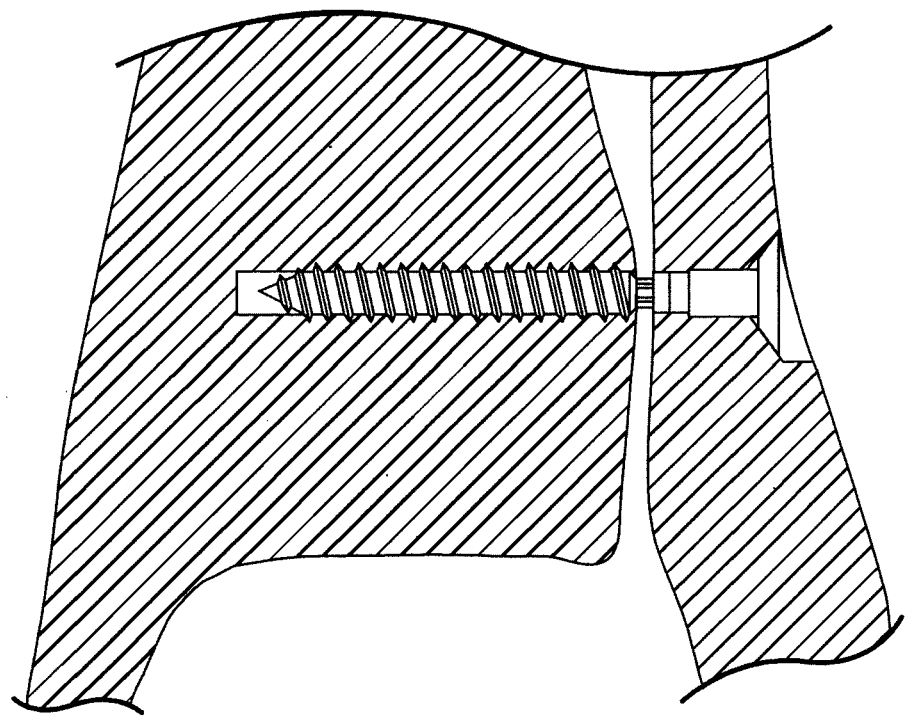
FIG. 21 is a schematic depiction of another implantable syndesmosis injury treatment device implanted in a patient in which the distance between the tibia and fibula has been reduced, according to one embodiment.

As discussed above, one advantage of various embodiments disclosed herein is the ability to adjust the tension of the device 10, thereby resulting in the adjustment of the distance between the tibia 2 and the fibula 4. This adjustment capability is shown in FIGS. 20 and 21. FIG. 20 shows the device 10 implanted such that there is a gap between the tibia 2 and fibula 4. If it is desirable to reduce that gap, the second anchor 14 can be rotated to reduce the length of the tether 16, thereby urging the tibia 2 and fibula 4 closer together and reducing the gap between them as shown in FIG. 21.

Figure 22:
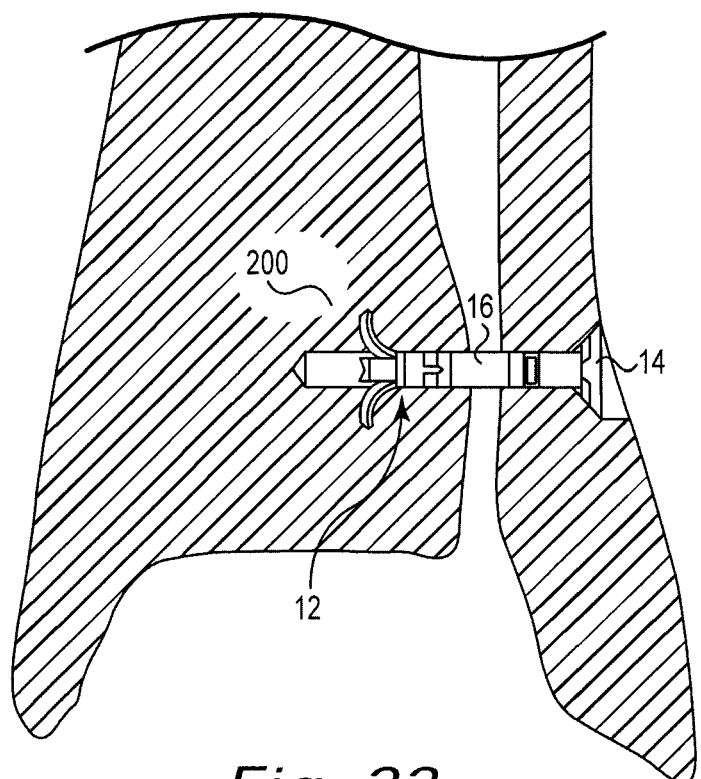
FIG. 22 is a schematic depiction of an alternative implantable syndesmosis injury treatment device having deployable prongs implanted in a patient, according to one embodiment.

An alternative device 200 is depicted in FIG. 22. This device has a first anchor 12 that is a pronged anchor 12 similar to that shown in FIG. 4 above. In this embodiment, the first anchor 12 can be deployed in the tibia 2 by any known method of deploying a pronged anchor. According to one implementation, the pronged anchor 12 can be deployed using methods similar to those disclosed in U.S. application Ser. No. 12/793,429, discussed and incorporated by reference above.

Figure 23A:
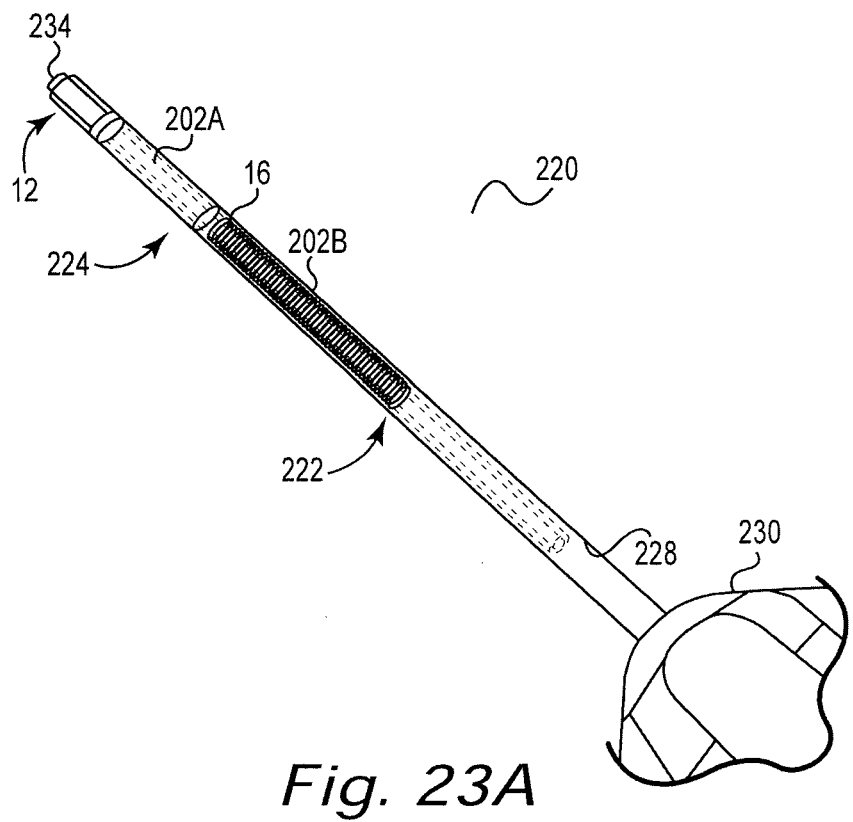
FIG. 23A is a perspective, cutaway view of a deployment tool and first anchor having deployable prongs, according to an alternative embodiment.
Figure 23B:
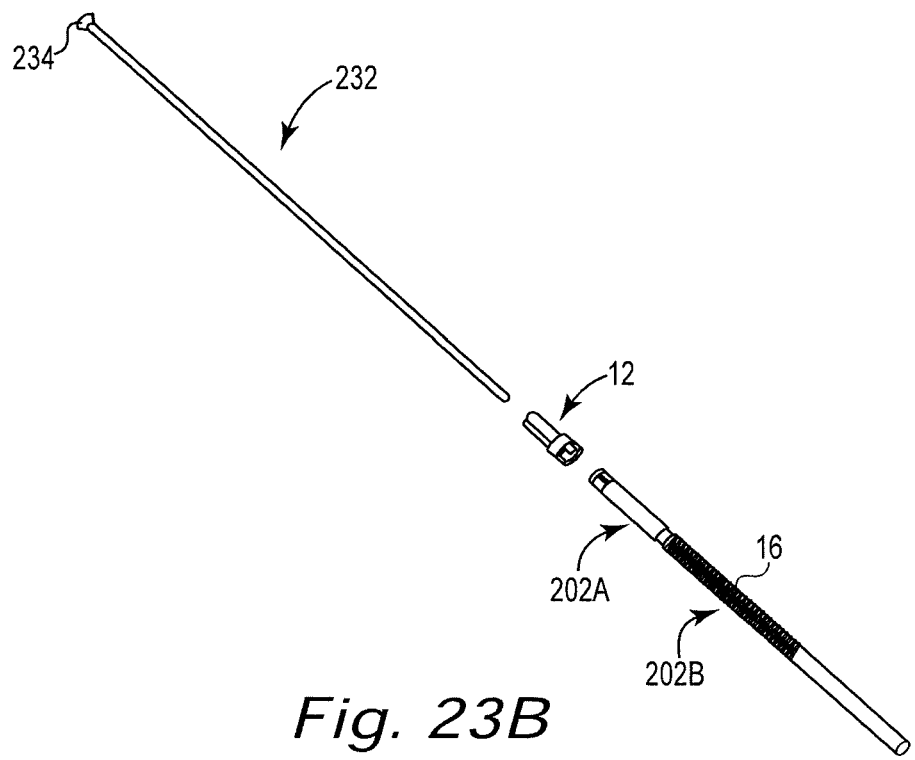
FIG. 23B is a perspective view of various parts of the deployment tool and first anchor depicted in FIG. 23A, according to one embodiment.

One exemplary embodiment of the device 200 and implantation tool 220 and the related methods for implanting the device 200 (as shown in FIG. 22) are depicted in further detail in FIGS. 23A-23F. As best shown in FIGS. 22, 23A, and 23B, the device 200 has an expandable pronged first anchor 12, a tether 16, and a second anchor 14. In some embodiments, the pronged first anchor 12 can be similar to the anchor 12 depicted in FIG. 4. The first anchor 12 is coupled to the tether 16. The tether 16 has a non-threaded component 202A and a threaded component 202B. In one embodiment, the non-threaded component 202A is a flexible component 202A. Alternatively, the non-threaded component 20A can be a substantially rigid component 202A.

The tool 220 has a tool body 222 with a distal end 224 having prongs 226 as best shown in FIG. 12C. The distal end 224 with the prongs 226 further defines an opening (not shown) in fluid communication with a lumen 228 (as best shown in FIG. 23A) that is defined within the tool body 222 and runs along the entire length of the tool body 222. The tool 220 also has a handle 230 coupled at the proximal end of the tool body 222.

Figure 23C:
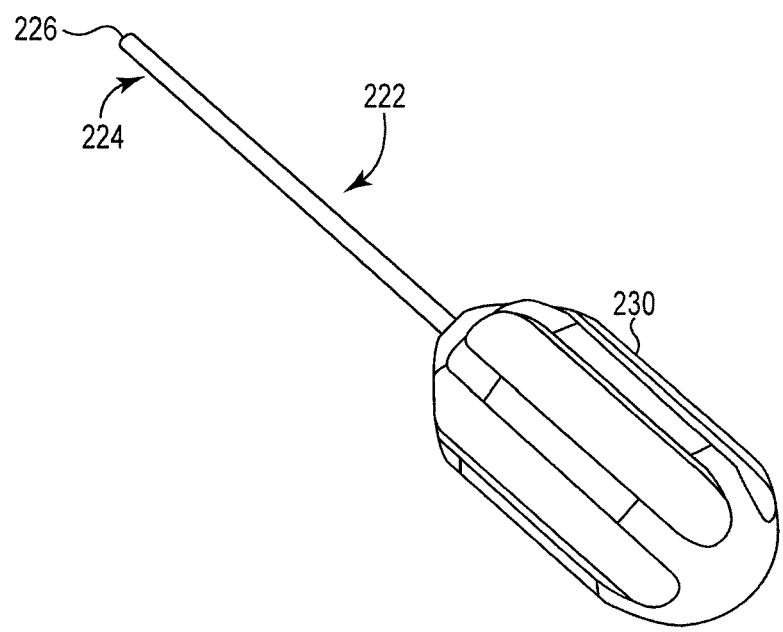
FIG. 23C is a perspective view of the deployment tool of FIG. 23A, according to one embodiment.
Figure 23D:
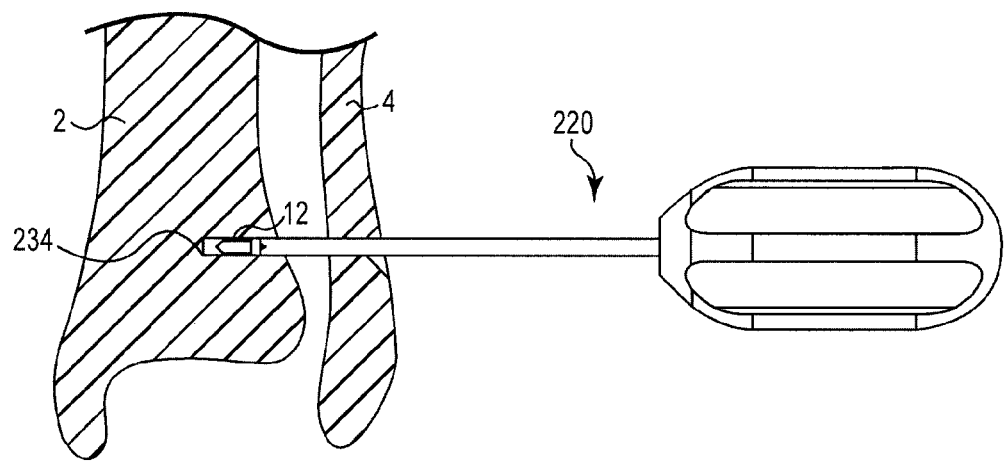
FIG. 23D is a schematic depiction of the first anchor and deployment tool of FIG. 23A positioned in a tibia and fibula, according to one embodiment.

Prior to implantation, the distal end 224 of the tool body 222 is coupled to the proximal end of the first anchor 12 as best shown in FIG. 23D. That is, the prongs 226 are configured to be engageable with the anchor 12. As best shown in FIGS. 23A-23C, prior to implantation, the tool 220 also contains the tether 16. That is, prior to implantation, the tether 16 is disposed within the lumen 228 of the tool body 222 and coupled to the first anchor 12. In addition, prior to implantation, a deployment component 232 is disposed through a lumen in the first anchor 12 and tether 16. The deployment component 232 has a deployment anvil 234 at the distal end of the deployment component 232. According to one embodiment, the deployment component can be used to "deploy" the pronged first anchor 12, urging the anchor 12 from the un-deployed to the deployed configuration.

Figure 23E:
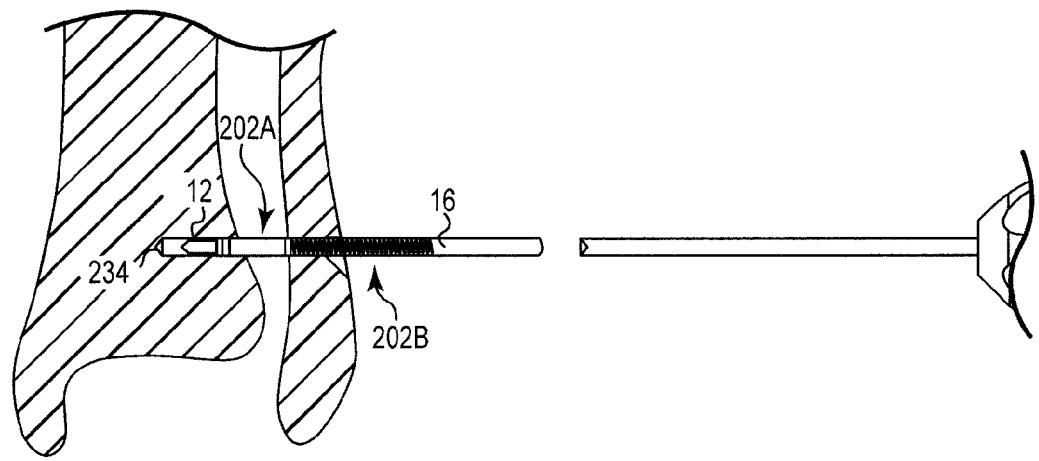
FIG. 23E is a schematic depiction of the first anchor and tether of FIG. 23A positioned in a tibia and fibula with the deployment tool being removed, according to one embodiment.

According to one embodiment, the device 200 can be implanted by positioning the first anchor 12 through the fibula 4 and to the desired depth in the tibia 2 with the implantation tool 220, as best shown in FIG. 23D. Upon placement of the first anchor 12 to the desired depth, the implantation tool 220 is retracted as shown in FIG. 23E, leaving the first anchor 12 implanted in the tibia 2 and the tether 16 coupled to the first anchor 12 and disposed through the hole in the fibula 4. At this point, the deployment component 232 is still disposed through the first anchor 12 and tether 16 and extends proximally from the tether 16. To deploy the anchor 12, the user can pull the deployment component 232 proximally in relation to the anchor 12 and tether 16, either manually or using a deployment tool (not shown) similar to that disclosed in U.S. application Ser. No. 12/793,429, discussed and incorporated by reference above. Urging the device 232 in the proximal direction urges the anvil 234 in the proximal direction, thereby forcing the prongs of the first anchor 12 into the deployed configuration in a fashion similar to that disclosed in U.S. application Ser. No. 12/793,429. In addition, according to certain embodiments, when the prongs reach the fully deployed configuration, further pulling of the device 232 causes a designed fracture point (not shown) on the device 232 to exceed its maximum tolerance, thereby causing the tool 232 to fracture, allowing the user to remove the device 232 while only the anvil 234 remains in the device 200.

Figure 23F:
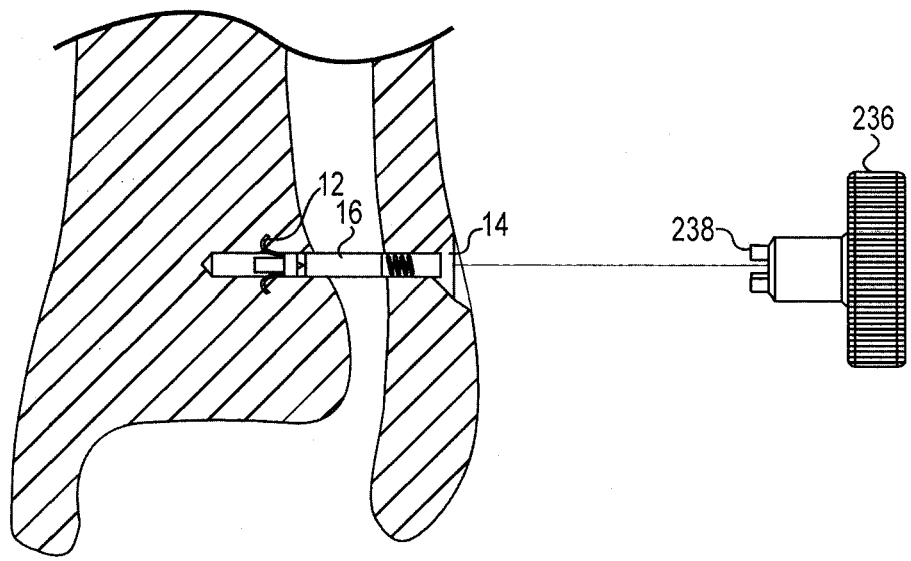
FIG. 23F is a schematic depiction of the implantable device of FIG. 23A implanted in the tibia and fibula with the anchor driving tool being removed, according to one embodiment.

Once the implantation tool 220 is retracted and the first anchor 12 is deployed, the second anchor 14 can be positioned over and attached to the tether 16, as best shown in FIG. 23F. The second anchor 14 can be an anchor 14 such as those depicted in FIGS. 6A and 6B and described in detail above. In one embodiment, the second anchor 14 can be coupled to the tether 16 using a driver tool 236 as shown in FIG. 23F. The driver tool 236 can be similar to the driver tool 160 described above. In use, the anchor 14 and tool 236 are inserted over the tether 16 and the anchor 14 is advanced distally along the tether 16 until the anchor 14 reaches the threads 202B on the tether 16. When the anchor 14 comes into contact with the threads 202B on the tether 16, the user rotates the driver tool 236 to continue to advance the anchor 14 distally along the tether 16. The anchor 14 is advanced until it reaches the desirable position with respect to the fibula 4.

Once the anchor 14 has been positioned as desired, the driver tool 236 is removed, as best shown in FIG. 23F. In some embodiments, upon removal of the tool 236, a portion of the tether 16 extends proximally from the anchor 14. According to one embodiment, that portion can be removed using a cutting tool (not shown) similar to the tool depicted in FIG. 18 using similar methods. Once the excess portion of the tether 16 is removed, the device 200 is fully implanted as shown best in FIG. 22.

In one implementation, at least a portion of the tether 16 in the device 200 is made of bio-absorbable material. For example, according to one embodiment, the bio-absorbable portion of the tether 16 is the portion that spans the syndesmotic gap between the tibia 2 and the fibula 4. In such an embodiment, the bio-absorbable portion of the tether 16 would provide substantially rigid or semi-rigid fixation during the healing period but enhance flexibility after healing was complete, because the bio-absorbable portion would ultimately be absorbed.

In a further alternative embodiment, the device 200 has a flexible tether 16. More specifically, the tether 16 can be made of a flexible material, such as, for example, a flexible polymeric material. In certain implementations, the tether 16 can be a solid flexible polymer, a combination of several smaller flexible elements, a series of suture lines, or any other known flexible configuration. It is further understood that the tether 16 in the device 200 can be any tether configuration or material as described throughout this application.

Figure 24:
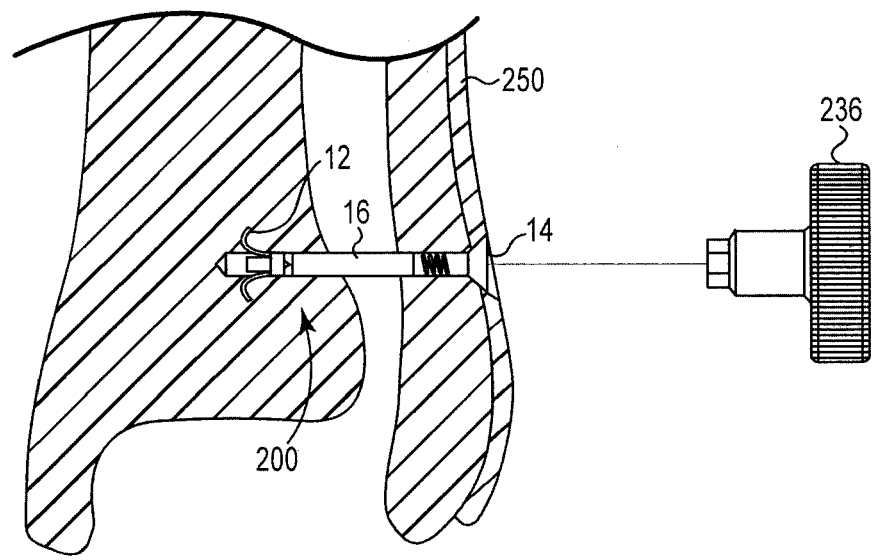
FIG. 24 is a schematic depiction of another implantable device implanted in the tibia and fibula through a fixation plate with the anchor driving tool being removed, according to another embodiment.

According to a further alternative embodiment as shown in FIG. 24, the device 200 (or any other implantable device contemplated herein) can be implanted using a fracture fixation plate 250. It is further understood that various embodiments disclosed and contemplated herein can be used with any known fixation device positioned along either the tibia 2 or fibula 4 or both for purposes of stabilizing the bone(s).

Figure 25:
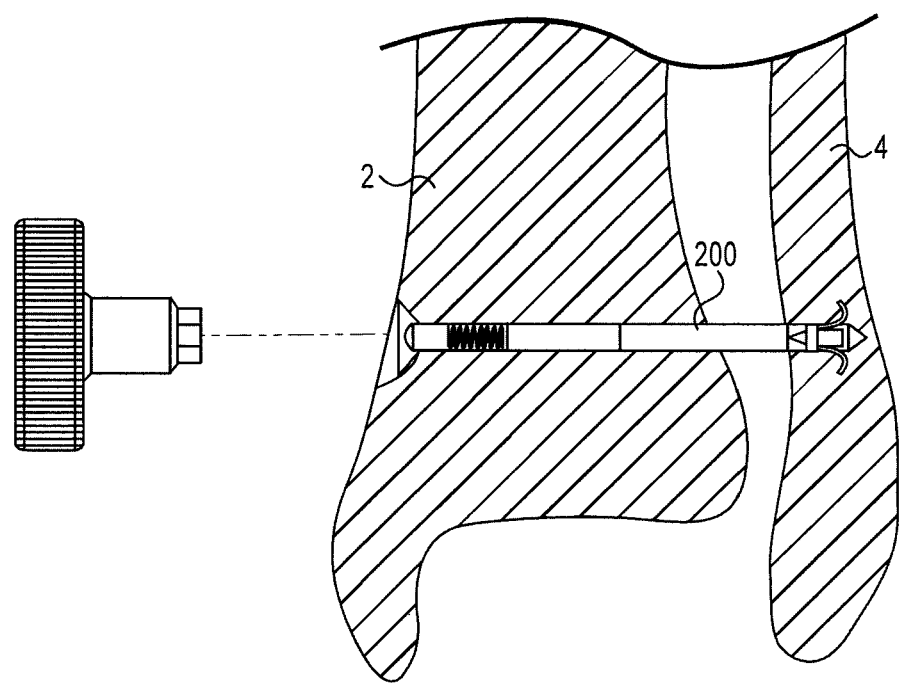
FIG. 25 is a schematic depiction of another implantable device implanted in the tibia and fibula in a reverse orientation in comparison to the prior embodiments with the anchor driving tool being removed, according to another alternative embodiment.

In another alternative implementation, the device 200 can be implanted through the tibia 2 and into the fibula 4, as best shown in FIG. 25 (in a "reverse orientation" in contrast to implantation through the fibula 4 and into the tibia, which is described in detail above and elsewhere herein). It is further understood that the various methods and devices described herein can be used to implant any device contemplated herein in such a reverse orientation. According to certain embodiments, the reverse orientation can result in no protrusion on the fibula 4 (in comparison to the other embodiments described above) or can be employed when there is no fracture in the fibula 4.

Figure 26A:
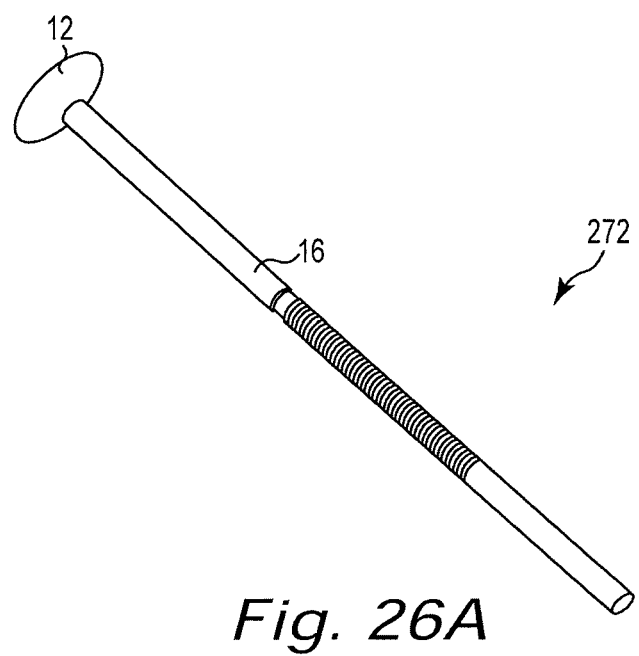
FIG. 26A is a perspective view of a first anchor and tether, according to yet another alternative embodiment.

A further alternative embodiment is shown in FIGS. 26A-26E. In accordance with one implementation, this device 270 can be implanted using a different method than that described above. In this embodiment, the first anchor 12 and the tether 16 are a single, unitary component 272, as best shown in FIG. 26A, in which the first anchor 12 is a button anchor 12. That is, the anchor 12 and tether 16 are permanently attached in a component 272 that is comprised of a long tubular member 16 having a head 12 at the proximal end. Alternatively, the anchor 12 and tether 16 can be separate components.

In one embodiment, the tether 16 is a threaded rod 16 as shown. The tether 16 can be made of a fully or partially polymeric material. Alternatively, the tether 16 can be made entirely or at least partially of a bio-absorbable material. In a further alternative, the tether 16 can be made of any of the materials described with respect to the tether 16 depicted in FIGS. 5A-5E and described above.

Figure 26B:
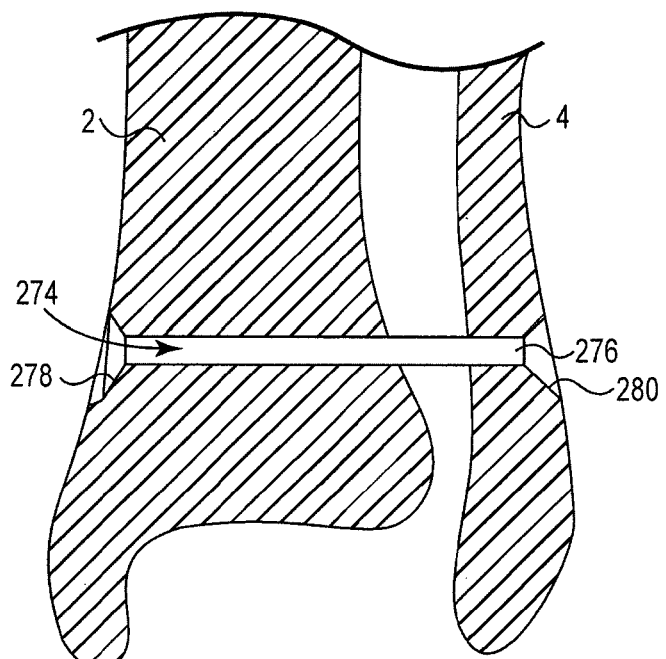
FIG. 26B is a schematic depiction of holes in the tibia and fibula, according to a further alternative embodiment.

In use, holes are drilled through the entire width of both the tibia 2 and the fibula 4, resulting in a hole 274 that extends through the tibia 2 and a hole 276 that extends through the fibula 4, as best shown in FIG. 26B. According to one embodiment, countersink holes 278, 280 are formed near the bone surface of both holes 274, 276 as shown, with the holes 278,280 being configured to receive the button anchor 12 and the second anchor 14 (as shown in FIG. 26D). Alternatively, counterbore holes can be formed. In a further alternative, the button anchor 12 is configured to have a thin or otherwise minimal profile that allows it to be positioned on the surface of the medial aspect of the tibia 2 without the need for a countersink hole. For example, in one implementation, the button anchor 12 can have a rounded configuration that allows it to be positioned on the surface of the tibia while minimizing the protrusion caused by the anchor 12. In one alternative embodiment, the button 12 can be made of a flexible material, thereby resulting in greater flexibility and angular rotational freedom for the overall construct. In one implementation, an anchor 14 made of flexible material allows the surgeon to tailor the system flexibility to the needs of the patient, because, for example, different patients can exhibit different levels of baseline fibula rotation. For example, in one embodiment, the button 12 can be made of silicone or any other known flexible material for use in implantable medical devices.

Figure 26C:
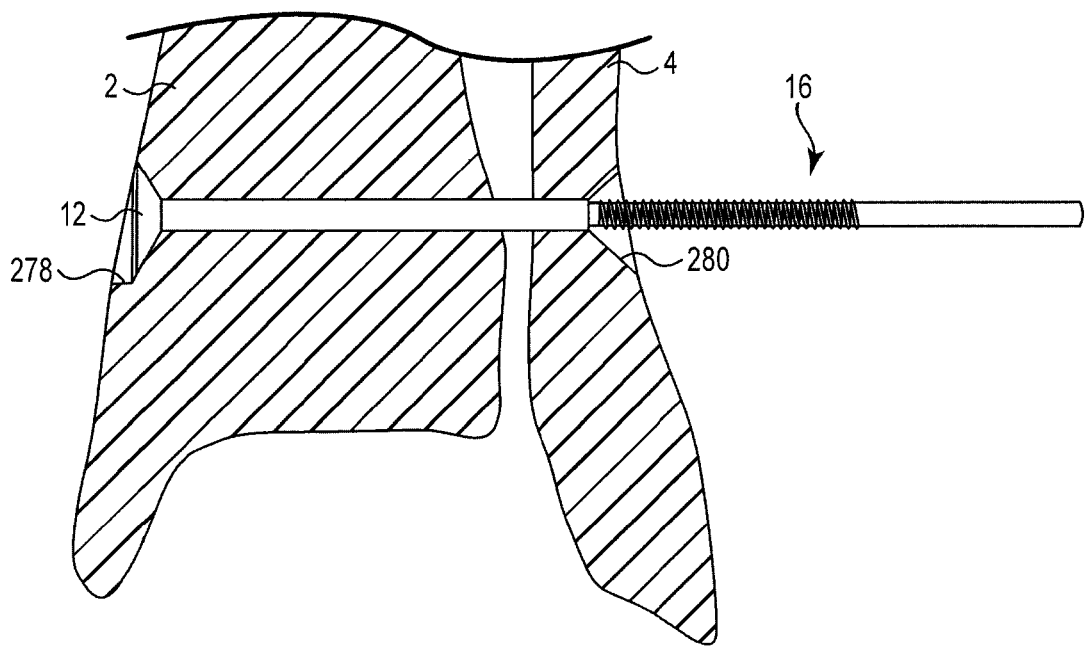
FIG. 26C is a schematic depiction of the first anchor and tether of FIG. 26A positioned through a tibia and fibula, according to one embodiment.
Figure 26D:
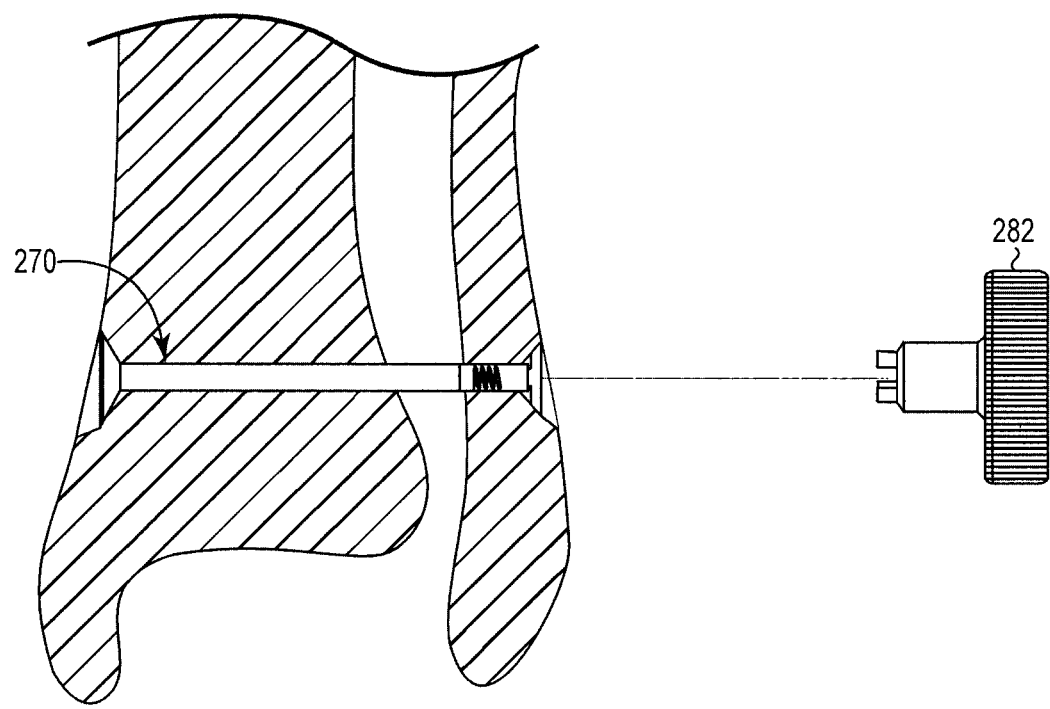
FIG. 26D is a schematic depiction of the first anchor and tether of FIG. 26A implanted with a second anchor into a tibia and fibula with the anchor driving tool being removed, according to one embodiment.

As best shown in FIG. 26C, the component 272 is positioned through the holes 274, 276 with the first anchor 12 positioned in the countersink 278 in the tibia 2. Once the component 272 is positioned as desired, the second anchor 14 can positioned over the distal end of the tether 16 and urged along the tether 16 (perhaps using a driver tool 282 as shown in 26D) until the anchor 14 is positioned against the fibula 4 as desired. When the second anchor 14 is in position, any portion of the tether 16 that extends beyond the second anchor 14 away from the bones can be removed. In one embodiment, the excess portion is removed using a cutter such as the cutter 180 described above. Once the excess portion is removed, the device 270 is implanted, as shown in FIG. 26D.

Although the present invention has been described with reference to preferred embodiments, persons skilled in the art will recognize that changes may be made in form and detail without departing from the spirit and scope of the invention.

What is claimed is:

1. A method of treating a syndesmosis injury, comprising:
   forming a hole through a second bone and into a first bone;
   inserting a deployment assembly into the hole in the second bone, the deployment assembly comprising:
   (a) an outer tube having a distal end, a proximal end, an outer diameter, and an inner diameter
   (b) a tether disposed within the outer tube, the tether comprising:
      (i) a flexible component; and
      (ii) a base component coupled to the flexible component, said base component being substantially rigid, the base component having a distal portion that is externally threaded having a base component external thread having a base component external thread major diameter, and having a proximal portion; and
   (c) a first bone anchor disposed at a distal end of the outer tube, the first bone anchor having a first bone anchor external thread having a first bone anchor external thread major diameter, the first bone anchor being coupled to a distal end of the flexible component, wherein the outer tube has a torque-transmitting engagement feature cooperating with the first bone anchor;
   positioning the first bone anchor in the first bone;
   removing the outer tube; and
   coupling a second anchor to the base component and positioning the second anchor in the second bone or in a plate connected to the second bone,
wherein the first bone anchor external thread major diameter is greater than the outer tube outer diameter at the distal end, the outer tube outer diameter is greater than the outer tube inner diameter, the outer tube inner diameter is greater than the base component external thread major diameter, and the base component proximal portion is sufficiently narrow so that the second anchor can advance non-rotatingly along the proximal portion of the base component.

2. The method of claim 1, wherein the positioning the first bone anchor further comprises rotating the deployment assembly to screw the first bone anchor into the first bone.

3. The method of claim 1, further comprising urging the second anchor distally in relation to the tether, wherein urging the second anchor distally comprises sliding the second anchor distally along the proximal portion of the base component, followed by engaging an internal thread of the second anchor with the base component external thread, followed by rotating the second anchor with respect to the base component to further advance the second anchor distally, and further comprising severing an extending portion of the base component so that a remaining portion of the base component does not protrude beyond the second anchor.

4. The method of claim 1, further comprising first positioning a guide wire through the second bone and into the first bone, wherein the forming the hole in the second bone further comprises positioning a drill over the guide wire and drilling the hole in the second bone.

5. A method of treating a syndesmosis injury, comprising:
forming a hole through a second bone and into a first bone;
inserting an implantation tool comprising a deployment assembly into said hole in said second bone, said deployment assembly comprising:
a first bone anchor, said first anchor being suitable for placement in said first bone, said first bone anchor having a first anchor external thread having a first anchor external thread major diameter, said first bone anchor having at its proximal end a coupling feature;
an outer tube having a lumen therewithin and having, at its distal end, a protrusion capable of being received in said coupling feature of said first anchor;
a tether comprising a flexible component coupled to said first bone anchor and a base component coupled to said flexible component, said base component being substantially rigid,
wherein when the outer tube is coupled with the first bone anchor said first bone anchor is disposed distally of said outer tube and said base component is contained entirely within said lumen of said outer tube and does not extend beyond a proximal end of the implantation tool;
positioning said first bone anchor in said first bone;
removing said outer tube; and
coupling a second anchor to a proximal end of said base component and positioning said second anchor in said second bone or in a plate connected to said second bone,
wherein a distal portion of the base component has an external thread and a proximal portion of the base component is unthreaded, and wherein the second anchor has an internal thread engageable with the external thread of the base component, and wherein the unthreaded portion of the base component is sufficiently long so that when the second anchor, while engaged with a driver tool having a central bore therethrough, begins to engage the external thread of the base component, some of the base component protrudes proximally from the driver tool.

6. The method of claim 5, further comprising first positioning a guide wire through said second bone and into said first bone, wherein the forming said hole in said second bone further comprises positioning a drill over said guide wire and drilling said hole in said second bone.

7. The method of claim 5, wherein the positioning said first bone anchor in said first bone further comprises rotating said deployment assembly to screw said first bone anchor into said first bone.

8. The method of claim 5, wherein positioning said first bone anchor into said first bone further comprises positioning said first bone anchor into said first bone such that said proximal end of said first bone anchor is substantially flush with a surface of said first bone.

9. The method of claim 5, further comprising, after said coupling said second anchor to said proximal end of said base component, urging said second anchor distally in relation to said tether, thereby urging said second anchor toward said first borne anchor.

10. The method of claim 9, wherein urging the second anchor distally in relation to the tether further comprises rotating the second anchor with respect to said base component.

11. The method of claim 5, wherein said flexible component comprises a suture.

12. The method of claim 5, wherein said flexible component comprises a resorbable suture.

13. The method of claim 5, wherein said flexible component has a strength such that said flexible component fails before either said first bone anchor or said second anchor is pulled from a respective implantation site.

14. The method of claim 5, wherein said outer tube does not extend radially beyond said major diameter of said external threads of said first bone anchor.

15. The method of claim 5, further comprising:
examining a radiographic image to determine an initial position of said second bone in relation to said first bone; and
adjusting the positioning of said second anchor based on said initial position of said second bone in relation to said first bone to achieve a desired position.

16. The method of claim 5, further comprising:
evaluating ankle function to determine an initial position of said second bone in relation to said first bone; and
adjusting the positioning of the second anchor based on the initial position of said second bone in relation to the first bone to achieve a desired position.

17. The method of claim 5, wherein said first bone is the tibia bone and said second bone is the fibula bone.

18. A method of treating a syndesmosis injury, comprising:
forming a hole through a second bone and into a first bone;
inserting a deployment assembly into said hole in said second bone, said deployment assembly comprising:
a first anchor, said first anchor being suitable for placement in said first bone, said first anchor being distally located;
a tether, said tether comprising a flexible component and a base component, wherein said base component is substantially rigid, wherein said first anchor is coupled to said flexible component, and said flexible component is coupled to said base component, and said base component extends more proximally than said flexible component, and wherein said base component has an external thread and a proximal portion of the base component is unthreaded;
positioning said first anchor in said first bone; and
coupling a second anchor to a proximal end of said base component, wherein said second anchor has an internal thread complementary to said base component external thread; and
positioning said second anchor in said second bone or in a plate connected to said second bone,
wherein the unthreaded portion of the base component is sufficiently long so that when the second anchor, while engaged with a driver tool having a central bore therethrough, begins to engage the external thread of the base component, some of the base component protrudes proximally from the driver tool.

19. The method of claim 18, further comprising removing an excess length from said proximal portion of said base component.

20. The method of claim 18, wherein positioning said second anchor in said second bone comprises rotating said second bone anchor with respect to said base component.

21. The method of claim 18, wherein said flexible component comprises a resorbable suture.

22. The method of claim 18, further comprising, after said positioning said second anchor in said second bone, evaluating a relative position of said bones, and re-positioning said second anchor to achieve desired positioning of said bones.

23. The method of claim 18, wherein said second anchor comprises a head having a curved underside of said head between a top of said head and a body of said second anchor, wherein said curved underside has a shape that corresponds to a shape of a hole in said plate.

24. A method of treating a syndesmosis injury, comprising:
forming a hole through a second bone and into a first bone;
inserting a deployment assembly into said hole in said second bone, said deployment assembly comprising:
an outer tube having an outer diameter and an inner diameter and having a lumen therewithin and having, at its distal end, a protrusion;
a first anchor located distally of said distal end of said outer tube, said first anchor being suitable for placement in said first bone, said first anchor having an external thread having a major diameter, said first anchor having a coupling feature located within said major diameter and capable of receiving said protrusion of said outer tube;
a tether comprising a flexible component coupled to said first anchor and a base component coupled to said flexible component, said base component being substantially rigid,
wherein some of said base component is more proximal than said flexible component,
wherein said base component has a base component external thread,
wherein said base component fits inside said lumen of said outer tube;
positioning said first anchor in said first bone, wherein said positioning comprises applying torque to said outer tube causing rotation and advancement in a distal direction of said first anchor;
withdrawing said outer tube in a proximal direction while said flexible component remains coupled to said first anchor and said base component remains coupled to said flexible component; and
coupling a second anchor to said base component and positioning said second anchor in said second bone or in a plate connected to said second bone, wherein said second anchor has an internal thread complementary to said base component external thread, wherein said coupling includes rotating said second anchor with respect to said base component,
wherein the first bone anchor external thread major diameter is greater than the outer tube outer diameter at the distal end, the outer tube outer diameter is greater than the outer tube inner diameter, the outer tube inner diameter is greater than the base component external thread major diameter, and the base component further comprises a proximal portion that is sufficiently narrow so that the second bone anchor can advance non-rotatingly along the proximal portion of the base component.

* * * * *